(12) United States Patent
Syed et al.

(10) Patent No.: US 7,920,921 B2
(45) Date of Patent: Apr. 5, 2011

(54) ENDOSCOPIC DEVICE DELIVERY SYSTEM

(75) Inventors: Baber Syed, Cupertino, CA (US); Kurt Sparks, San Carlos, CA (US); Ken Wong, Saratoga, CA (US); Michael Wei, Redwood City, CA (US); Mir A. Imran, Los Altos Hills, CA (US)

(73) Assignee: IntraPace, Inc., Mountain View, CA (US)

( * ) Notice: Subject to any disclaimer, the term of this patent is extended or adjusted under 35 U.S.C. 154(b) by 914 days.

(21) Appl. No.: 11/766,660

(22) Filed: Jun. 21, 2007

(65) Prior Publication Data

US 2007/0299481 A1 Dec. 27, 2007

Related U.S. Application Data

(60) Provisional application No. 60/815,640, filed on Jun. 21, 2006.

(51) Int. Cl.
*A61N 1/05* (2006.01)
(52) U.S. Cl. ......................................... 607/40
(58) Field of Classification Search .............. 600/104, 600/114, 115, 121; 607/40, 41, 133; 606/174
See application file for complete search history.

(56) References Cited

U.S. PATENT DOCUMENTS

| | | |
|---|---|---|
| 6,535,764 B2 | 3/2003 | Imran et al. |
| 2005/0065571 A1 | 3/2005 | Imran |
| 2005/0143784 A1 | 6/2005 | Imran |
| 2006/0074457 A1 | 4/2006 | Imran et al. |
| 2006/0074458 A1 | 4/2006 | Imran |
| 2006/0111753 A1 | 5/2006 | Imran et al. |
| 2009/0287045 A1 * | 11/2009 | Mitelberg et al. ............. 600/104 |

OTHER PUBLICATIONS

U.S. Appl. No. 10/109,296, filed Mar. 26, 2002, Imran, et al.

* cited by examiner

*Primary Examiner* — Carl H Layno
*Assistant Examiner* — Brian T Gedeon
(74) *Attorney, Agent, or Firm* — Kilpatrick Townsend & Stockton LLP

(57) ABSTRACT

A system and method are disclosed for an implantable gastric stimulation system within the stomach. The stimulation system includes an electronics anchor, electrode lead anchor, implantable pulse generator and external programmer. The electronics anchor is configured to attach to the stomach wall at a first location and the electrode lead anchor configured to attach to the stomach wall at a second location. The electrode lead anchor includes one or more electrodes configured to contact the stomach wall and a flexible lead portion coupled to the one or more electrodes at one end with an the electrical connector portion at the other end. The implantable pulse generator has electronic circuitry and is attached to the electronics anchor; the electronic circuitry is connected to the electrical connector of the electrode lead anchor and can communicate with the one or more electrodes. The external programmer is used to communicate with the electronic circuitry of the pulse generator via a telemetry device to provide stimulation instructions to the pulse generator.

17 Claims, 19 Drawing Sheets

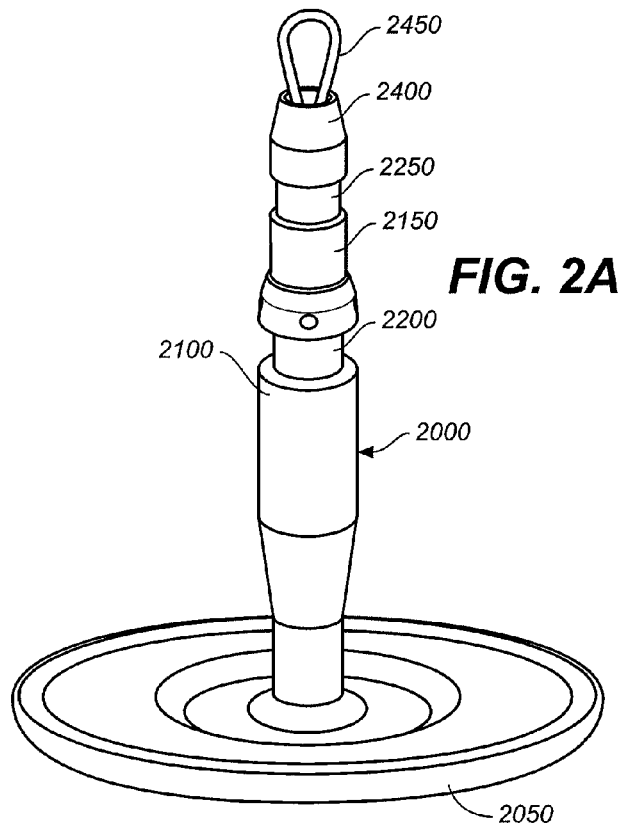
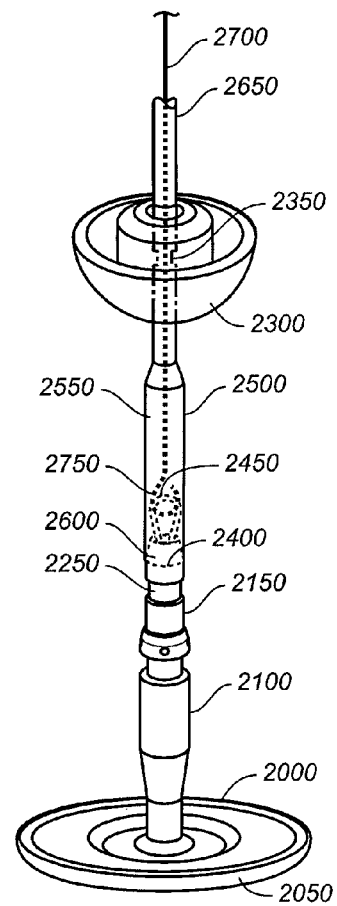

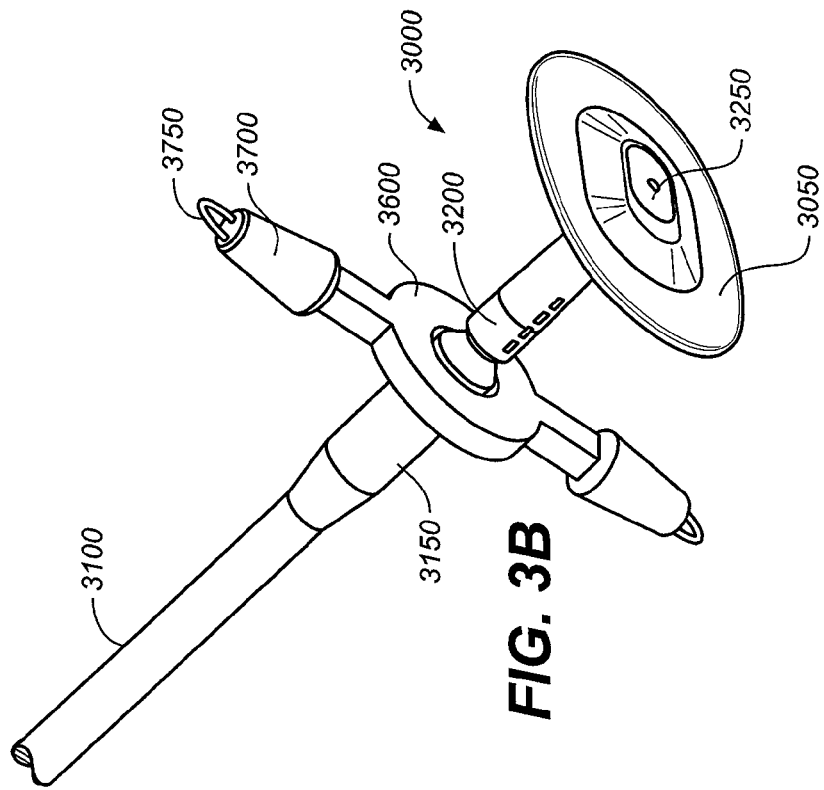
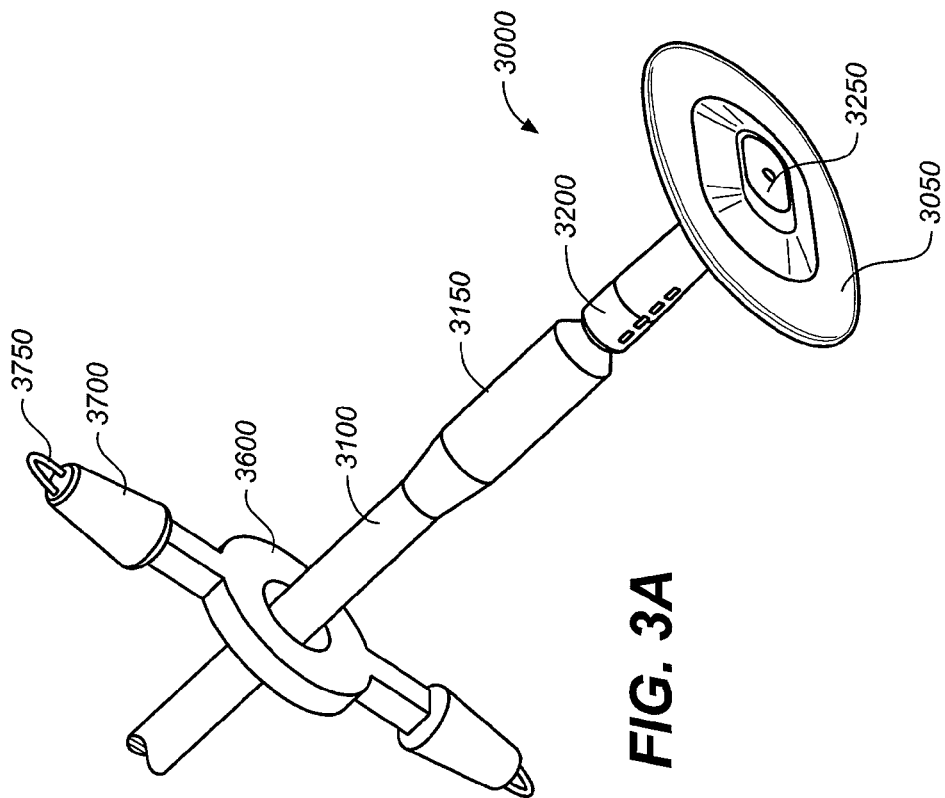

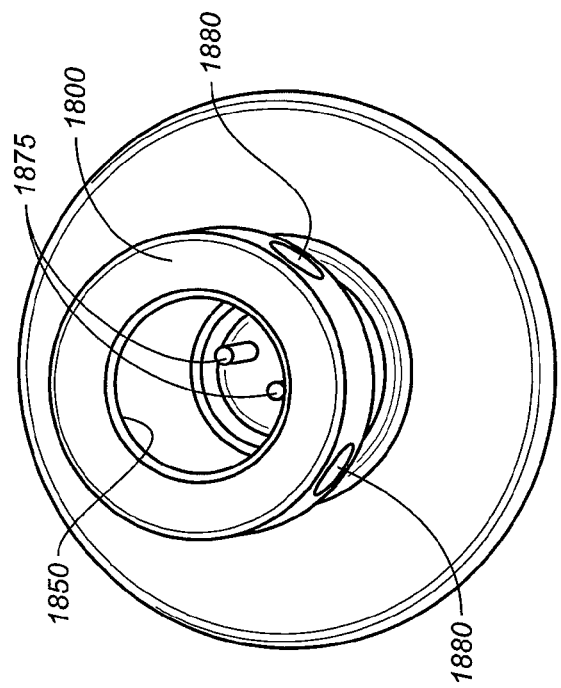
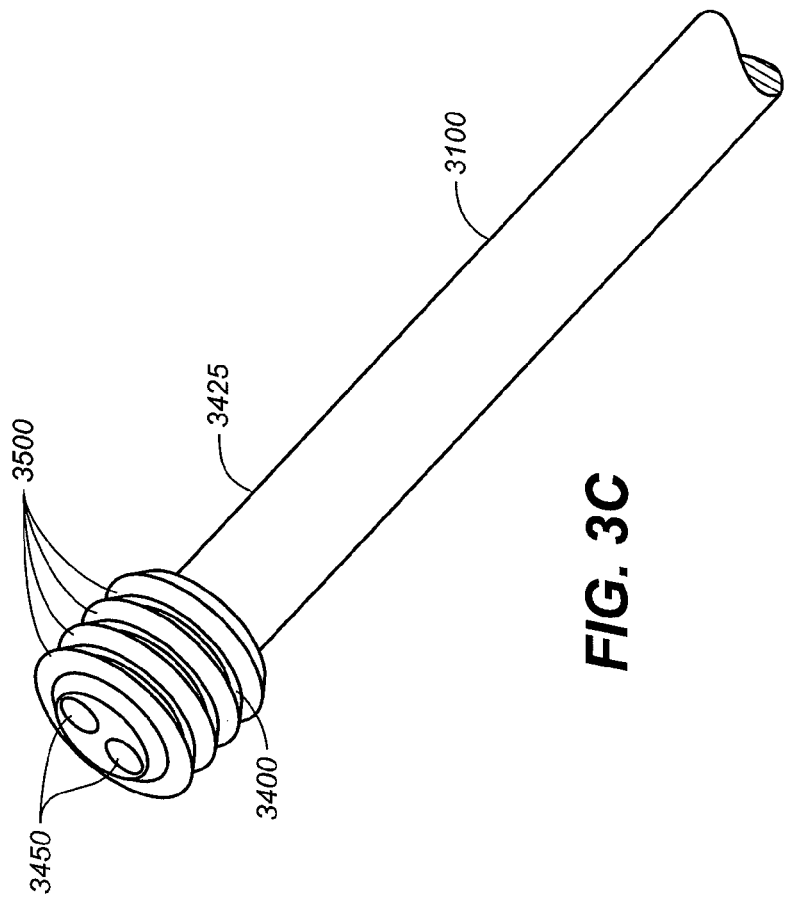
FIG. 3D
FIG. 3C

ENDOSCOPIC DEVICE DELIVERY SYSTEM

CROSS-REFERENCES TO RELATED APPLICATIONS

This application claims the benefit under 35 USC §119(e) of U.S. Provisional Patent Application 60/815,640 filed Jun. 21, 2006, the full disclosure of which is incorporated herein by reference.

BACKGROUND OF THE INVENTION

This invention relates to medical devices, systems, and methods. In exemplary embodiments, the invention provides an implantable device and system and method for implanting the device within a hollow organ. In other embodiments, the invention provides methods and devices for providing surgical access through a stomach or other tissue.

Electrical stimulation has been used to treat a variety of conditions within the human body. Electrical stimulation of the gastrointestinal tract, such as the stomach, small intestine and colon, have been used to treat a variety of gastric conditions, such as obesity, gastroparesis, gastric dysrhythmia, motility related disorders and nausea, to name a few. Obesity has become one of the leading causes of death in the United States. Electrical stimulation has been proposed to treat obesity by causing a feeling of satiety or reducing desire to eat.

Electrical stimulation has been proposed to treat motility related disorders by influencing contractile behavior. Various organs of the gastrointestinal tract such as the stomach, small intestine and colon contain cells that are believed to govern the organs' periodic contractile behavior. In healthy humans, in certain regions of the organs, these cells generate and propagate rhythmic electrical signals. In general, several types of electrical potential activity have been observed in the gastrointestinal tract. Consistent cyclic slow wave or pacesetter potentials have been observed and higher frequency spike activity has been observed that may correspond to some extent with smooth muscle contractile activity and peristalsis. The stomach and digestive system is also controlled by the nervous system that includes a highly complex enteric nervous system and to some extent, the central nervous system. It is believed that when the pacesetter potentials are combined with a chemical or neural excitation of the cells that smooth muscle contractile activity occurs. It is also believed that stimulation of the stomach may effect a subject's sensation of satiety through a complex system involving smooth muscle stimulation or contractions, and neural and chemical pathways.

An early attempt at a gastric stimulation device included an electrode at the end of a nasogastric tube or catheter. The nasogastric tube was passed into the stomach transnasally. Electrical stimulation was applied using an external stimulator unit through the electrode on the end of the tube. The return electrode was placed on the abdomen. This device required a transnasal procedure whenever stimulation was required.

Other devices used to pace the stomach have generally been implanted by accessing the outside of the stomach through an opening in the abdomen, either through open surgery or laparoscopic surgery. Electrodes have been attached to the stomach laparoscopically with attached leads extending through the abdomen to a subcutaneously or sub-muscularly implanted electronics unit. The devices may be anchored into the subcutaneous or sub-muscular pocket initially by a suture anchor and/or eventually by fibrous tissue ingrowth around the unit.

Endoscopic devices have been presented as an alternative to open or laparoscopic surgery. And example of such devices are described, for example in related U.S. Pat. No. 6,535,764, fully incorporated herein by reference. U.S. Pat. No. 6,535,764 describes a gastric stimulator that is implanted by delivering the device through the esophagus of a subject and attaching to the stomach wall from the inside of the stomach. Also, related U.S. patent application Ser. No. 10/109,296, fully incorporated herein by reference, describes a gastric stimulator that is implanted sub-mucosally within the stomach wall.

It would be desirable to provide improved gastric stimulation devices, delivery systems and delivery methods for an endoscopic approach. Such devices, systems and methods should efficiently access the implantation site through the esophagus, should allow secure attachment of the stimulation device to the organ wall, and should provide desired stimulation to the organ wall. In addition, it would be desirable to provide delivery systems and methods for passing through the organ wall, such as to access the peritoneal cavity and/or fixedly attach devices to the organ wall. At least some of these objectives will be met by the present invention.

BRIEF SUMMARY OF THE INVENTION

The present invention provides an implantable gastric stimulation device and system or method for implanting such a device. The details of the invention are set forth below in the detailed description, drawings and/or claims.

BRIEF DESCRIPTION OF THE DRAWINGS

FIG. 2A is a perspective view showing one embodiment of an electronics anchor.

FIG. 2B is a perspective view of the electronics anchor of FIG. 2A with a guide element guiding a retaining element.

FIG. 3A is a perspective view of an electrode anchor and retaining element in accordance with one embodiment of the invention.

FIG. 3B is a perspective view of the electrode anchor with the retaining element in place.

FIG. 3C is a perspective view showing one embodiment of a connector end of an electrode lead.

FIG. 3D is a perspective end view showing one embodiment of a housing connector element configured to couple with the connector end of electrode lead of FIG. 3C.

DETAILED DESCRIPTION OF THE INVENTION

Figure 1:
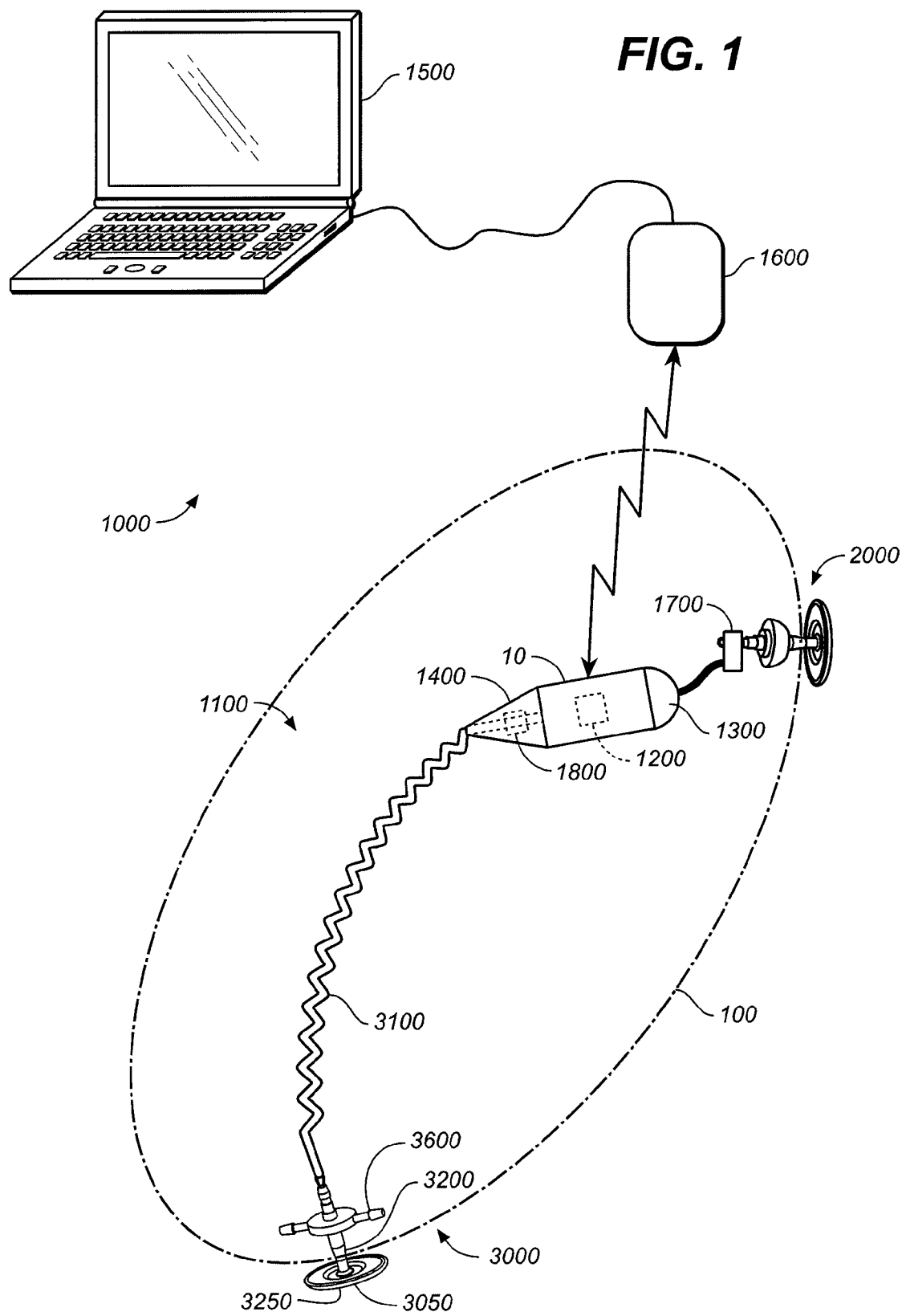
FIG. 1 is a schematic illustration showing one embodiment of a stimulation system implanted in a stomach.

FIG. 1 illustrates a stimulation system 1000 in accordance with one embodiment of the invention. In this embodiment, the stimulation system 1000 comprises a stimulator 1100 which is implantable within an organ, such as a stomach 100, small intestine or colon. The stimulator 1100 comprises an implantable pulse generator 10 and at least one stimulating electrode 3200. The implantable pulse generator (IPG) 10 comprises implantable electronic circuitry 1200 contained within a protective housing 1300. The housing 1300 is constructed of a corrosion resistant material, such as a material able to withstand implantation within a gastric environment. The IPG 10 is attached to the wall of the stomach 100 with the use of a housing anchor or electronics anchor 2000. The electronics anchor 2000 is typically attached to the wall of the stomach 100 in an area with less contractile forces, such as the fundus area. This assists in providing a relatively stable location for anchoring. However, stimulation may be desired in a different area, such as near the pes anserinus, along the lesser curvature or in desired locations throughout the antrum or body of the stomach. Therefore, an electrode may be positioned at any desired location with the use of an electrode lead anchor 3000. The electrode lead anchor 3000 has a flexible anchor portion 3050 that anchors the electrode lead anchor 3000 to the stomach wall adjacent a stimulation site. In this embodiment, the electrode lead anchor 3000 includes a first electrode 3200, a return electrode 3250 and flexible lead portion 3100. The flexible lead portion 3100 of the lead anchor 3000 is coupled to the electronic circuitry 1200 through a connector 1800 within header 1400 of housing 1300. The electrode lead anchor 3000 is configured to anchor the electrode 3200 so that it is in electrical contact with, or in proximity to the stomach wall. The flexible lead portion 3100 electrically couples the electrodes 3200, 3250 through the header 1400 to the electronic circuitry 1200. The electronic circuitry 1200 is configured to provide an electrically stimulating signal to the stomach wall through the electrodes 3200, 3250. While the electrodes 3200, 3250 are shown in particular configurations and locations on the electrode lead anchor 3000, numerous electrode configurations and positions are contemplated herein including, for example electrode constructs and configurations as set forth in U.S. Pat. No. 6,535,764 and related cases including but not limited to U.S. application Ser. Nos. 10/992,382; 11/256,264; 11/249,661; and 11/249,290, all of which are incorporated herein by reference.

An external programmer 1500 may be used to program various stimulation parameters or other instructions into a memory device included with the electronic circuitry 1200. In addition, the stimulation system 1100 may include sensors that sense one or more parameters related to the patient's physiology and/or diet. An example of electronic circuitry, stimulation parameters, sensors and related systems are described for example in U.S. Pat. No. 6,535,764 and U.S. patent application Ser. No. 10/950,345; all of which are incorporated herein by reference. The external programmer 1500 may be coupled to a telemetry device 1600 that communicates with the electronic circuitry for the above-described and other purposes.

Electronics Anchor

As mentioned above, the IPG 10 is anchored to the wall of the stomach 100 with the use of an electronics anchor 2000. FIGS. 2A-2D illustrate one embodiment of an electronics anchor 2000 in accordance with one aspect of the invention. The anchor 2000 illustrated in FIG. 2A comprises a flexible disc or distal anchor portion 2050 coupled to an elongate portion 2100. The anchor portion 2050 is configured to engage or oppose the serosal surface or outside of a stomach wall. The elongate portion 2100 is configured to extend through the stomach wall. The elongate portion 2100 includes a proximal portion 2150. The proximal portion 2150 typically resides within the stomach cavity and has a variety of features that are accessible from within the stomach. For instance, the proximal portion 2150 includes a plurality of detents, such as a first detent 2200. The first detent 2200 is used to receive a retaining element 2300, illustrated in FIG. 2B, and to hold the retaining element 2300 in place in relation to the anchor 2000. Thus, the retaining element 2300 has a detent mechanism 2350 which mates with the first detent 2200. The retaining element 2300 resides near or against the mucosal layer or inside surface of the wall of the stomach 100 so that the wall is held between the distal anchor portion 2050 and the retaining element 2300.

Figure 2C:
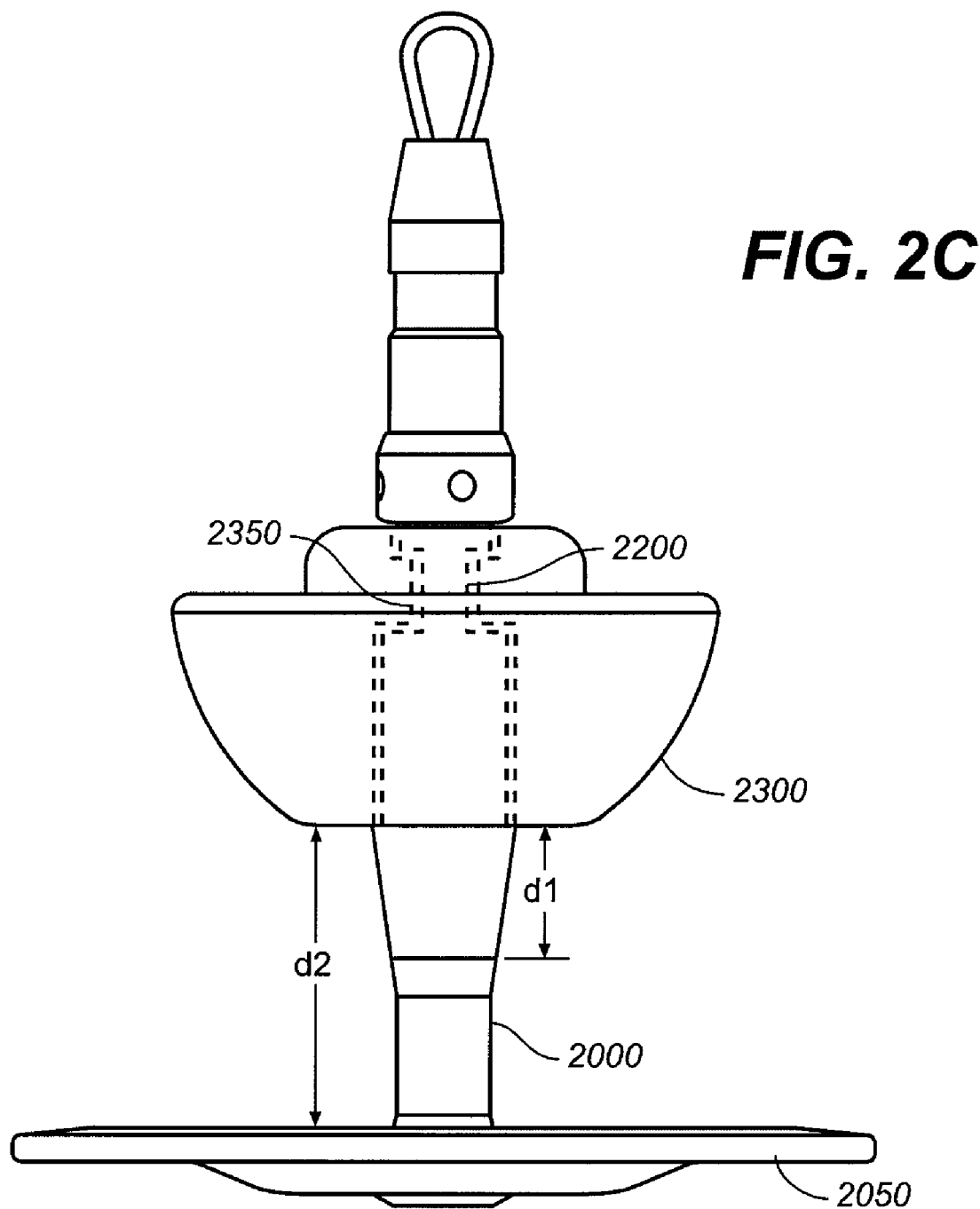
FIG. 2C is a side view of the anchoring device and retaining element of FIG. 2B with the retaining element in place.

FIG. 2C illustrates the retaining element 2300 locked into position on the elongate portion 2100 of the electronics anchor 2000. The retaining element 2300 includes a detent mechanism 2350 for engaging detent 2200. The retaining element 2300 is typically constructed of an elastomeric polymer material, such as a fluoroelastomer (e.g., Viton®, or Kalrez®), a fluorosilicone or a silicone. The detent mechanism 2350 of the retaining element 2300 may also be constructed of such a material. The detent mechanism 2350 lockingly engages the detent 2200 so that the retaining element 2300 is at a distance d2 from the distal anchor portion 2050. A distance d1 may be defined as a distance between the retaining element 2300 and the stomach wall (not shown) which is left after implantation and before healing occurs. The distance d2 is the distance from the inner surface of the anchor disc to the edge of the retaining element 2300. The distance d1 permits space for the increase of wall thickness of the stomach wall due to healing response of the stomach after the electronics anchor 2000 is implanted (see FIG. 5F). In other embodiments, there may not be a gap or distance d1 between the retaining element 2300 and stomach wall which allows some tissue compression between the retaining element 2300 and the distal anchor portion 2050. While not limited to these dimensions, a typical de novo stomach wall thickness in the region of the electronics anchor 2000 implantation may be from about 2 to 5 mm and after the stomach wall has healed around the anchor, the stomach wall thickness may typically range from about 5 to 15 mm. In the antrum portion of the stomach the de novo stomach wall thickness may range from 5 mm to 15 mm, and thickness after healing may typically range from 10 to 25 mm, but these dimensions are not so limited Referring back to FIG. 2B, one embodiment of installing the retaining element 2300 on the electronics anchor 2000 is illustrated. The electronics anchor 2000 further comprises a tapered end 2400 located on the proximal portion 2150 and a loop 2450 extending proximally out of the tapered end 2400. The loop 2450 may comprise a cable or other flexible tensile member, both ends of which are embedded into a generally cylindrically-shaped hub 2455 that may be welded into an opening at the terminal end of the proximal portion 2150 (see FIG. 2D). Embedding of the ends of the loop 2450 into the hub 2455 may be performed by swagging, welding or gluing, for example. In this embodiment, the hub and cable construction are welded into the proximal portion 2150 and the proximal portion subsequently insert molded into a polymer construct to form the electronics anchor 2000. The distal portion 2050 of the electronics anchor comprises a hub with a polymer disc insert molded over the hub. The distal anchor portion 2050 and the elongate portion 2100 of the electronics anchor 2000 between the distal anchor portion 2050 and the first detent 2200, are typically constructed of a corrosion resistant polymer such as a fluoroelastomer, e.g., Viton® or Kalrez®, both manufactured by Dupont Dow. This provides flexibility to the portion of the anchor that is positioned through the stomach wall and the interface between the distal anchor portion 2050 and the elongate portion 2100. In some embodiments, the more proximal portion 2150 including at least the first detent 2200 comprises a corrosion resistant metal such as, an alloy of Nickel, titanium and Cobalt, e.g., MP35N or MP35NLT manufactured by Fort Wayne Metals. This provides structure for connecting the retaining element 2300 and the connector element 1700 as described in more detail below. However, it may be understood that the electronics anchor 2000 may be comprised of a single material or a combination in any arrangement so as to achieve the desired results.

Referring again to FIG. 2B, the retaining element 2300 is installed on the electronics anchor 2000 with the use of a guide element 2500. Once the electronics anchor 2000 has been attached to the stomach wall (as will be described in detail in a later section), the guide element 2500 is attached to the elongate portion 2100 of the anchor 2000 from within the stomach cavity. The guide element 2500 is used to guide the retaining element 2300 to the anchor 2000. The guide element 2500 has a hook 2750 within its distal end 2550 which is extendable and couplable to the loop 2450 at tapered end 2400 of the electronics anchor 2000. The guide element 2500 includes an internal tapered wall 2600 defining an opening in its distal end 2550 for receiving the tapered end 2400 and loop 2450 of the proximal portion 2150 of the electronics anchor 2000. The guide element 2500 further includes a lumen 2650 extending axially therethrough and a tension element 2700 extending through lumen 2650 and having the hook 2750 at its distal end for hooking to loop 2450. The tapered wall 2600 matingly receives the tapered end 2400 of the electronics anchor 2000 and upon applying tension to the tension element 2700, the anchor 2000 is held firmly to the guide element 2500 and together they may act as a single element. Thus, the tension element 2700 may be manipulated from the proximal end of the guide element 2500 extending out of a subject's mouth, to hook and unhook the hook 2750 from the loop 2450 and/or to provide compression between the electronics anchor 2000 and the guide element 2500. The retaining element 2300 is configured to slide over the guide element 2500 and onto the electronics anchor 2000 such that the detent mechanism 2350 of the retaining element 2300 snaps into place onto the detent 2200. With the installment of the retaining element 2300, the stomach wall shall be positioned between the distal anchor portion 2050 and the retaining element 2300 so as to maintain contact between the distal anchor portion 2050 and the serosal surface of the stomach wall.

Figure 2D:
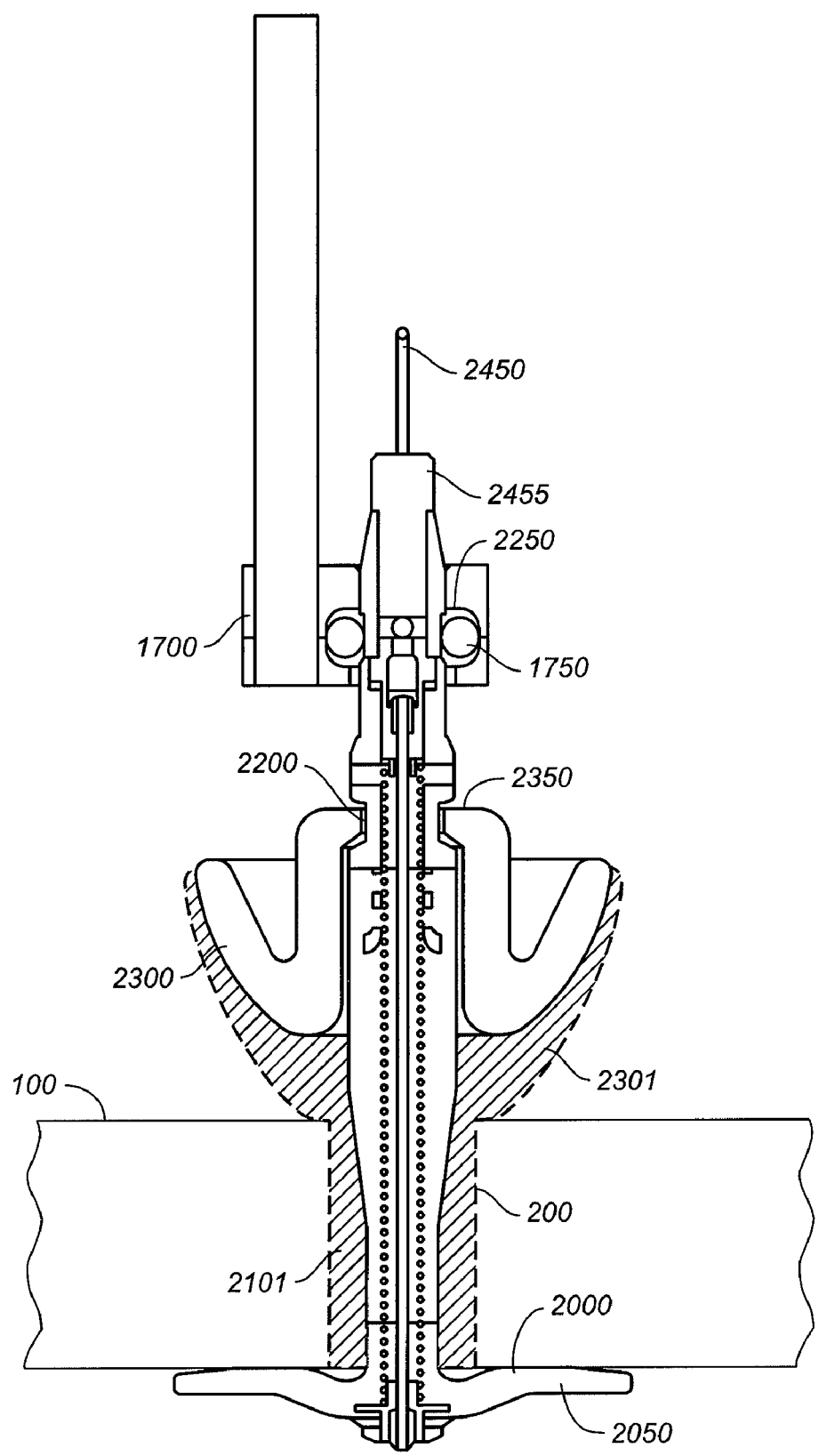
FIG. 2D is a side cross-sectional view of the anchoring device and retaining element with the electronics anchor connector attached.

FIG. 2D is a cross-sectional view showing the electronics anchor 2000 with the retaining element 2300 attached and the electronics anchor connector 1700 attached in a manner as described in more detail herein. Also shown in FIG. 2D is another embodiment of the retaining element 2300 having a dissolvable surface 2301 proximate the stomach wall 100. The dissolvable surface 2301 allows the retaining element 2300 to apply some tissue compression between the retaining element 2300 and the distal anchor portion 2050 during installation to seal the transgastric hole in the stomach wall. The dissolvable surfaces may be comprised of any material that will slowly dissolve in the gastric stomach environment, for example, the dissolvable surface may be silicone. Another embodiment of the elongate portion 2100 is also shown having a dissolvable surface 2101 so that the overall diameter is larger than the transgastric hole produced to deliver the distal anchor portion 3050 for deployment on the serosal surface of the stomach. The dissolvable surface 2101 thus assists in sealing the hole in the stomach wall. In another embodiment, the entire retaining element 2300 may be dissolvable. Once the fibrotic response forms a fibrotic capsule around the disc or distal anchor portion 2050 on the serosal surface or outside of a stomach wall, the retaining element 2300 may not be needed.

Electrode Lead Anchor

As mentioned previously, the at least one stimulating electrode 3200 electrically contacts the wall of the stomach 100 with the use of the electrode lead anchor 3000. FIGS. 3A-3B illustrate one embodiment of an electrode lead anchor 3000 having an anchor portion 3050; an elongate portion 3150; electrodes 3200, 3250; and a flexible lead portion 3100. The flexible lead portion 3100 connects the electrodes 3200, 3250 to the IPG 10 (not shown). A retaining element 3600 is positionable over the flexible lead portion 3100 portion (FIG. 3A) and the retaining element 3600 may be secured to the elongate portion 3150 within a detent in a manner similar to that described with respect to FIGS. 2A-2C above. Thus, the retaining element 3600 functions similarly to the retaining element 3200 of the electronics anchor 2000 by holding the wall of the stomach 100 between the retaining element 3600 and the anchor portion 3050. However, the retaining element 3600 of the electrode lead anchor 3000 has additional features that are used during the delivery and implantation steps of the present invention. For example, after the electrode lead anchor 3000 is attached to the stomach wall, the electrode lead anchor 3000 is left in place to allow tissue ingrowth and healing. Such healing stabilizes and strengthens the anchoring of the electrode lead anchor 3000 to the stomach wall. While such healing is occurring, the flexible lead portion 3100 is not attached to the IPG 10. To avoid possible entanglement of a free floating flexible lead portion 3100 within the stomach cavity, the flexible lead portion 3100 is attached to the retaining element 3600 during the healing process. The retaining element 3600 includes one or more arms 3700 with loop hooks 3750 for attaching the flexible lead portion 3100 thereto. Such attachment will be described and illustrated in a later section.

Referring now to FIG. 3C, the proximal end of the flexible lead portion 3100 is shown. The flexible lead portion 3100 is eventually joined with the IPG 10, as illustrated in FIG. 1. To make such a connection, the flexible lead portion 3100 has a connector end 3425 with a lead connector 3400, as illustrated in FIG. 3C. The lead connector 3400 is positioned on the connector end 3425 of the lead portion 3100 opposing the anchor portion 3050 on the other end. In one embodiment, the connector 3400 comprises female connectors 3450 and a plurality of sealing rings 3500 (FIG. 3C). The connector 3400 is designed to couple with the housing connector 1800 of the IPG 10. FIG. 3D shows one embodiment of the housing connector 1800 that includes a receiving portion 1850 configured for receiving the connector 3400 and engaging sealing rings 3500 within the bore of the receiving portion 1850. Male connectors 1875 within the housing connector 1800 electrically couple to the female connectors 3450 of the connector 3400. Once engaged, the electronic circuitry 1200 is electrically coupled to the electrodes 3200, 3250. Set screws 1880 within connector 1800 may be used to secure the housing connector 1800 to the lead connector 3400. In other embodiments, the connector 3400 and housing connector 1800 are IS-1 connectors commonly used in cardiac pacemaker designs.

Referring to FIGS. 4A-4P, 5A-5E and 6A-6F, systems and methods of producing a transgastric passageway through the stomach wall, accessing virtual space beyond the stomach wall (such as the peritoneal cavity), and implanting the electronics anchor 2000 and the electrode lead anchor 3000 are illustrated.

Accessing Space Adjacent the Serosa of the Stomach Through the Esophagus

Figure 4A:
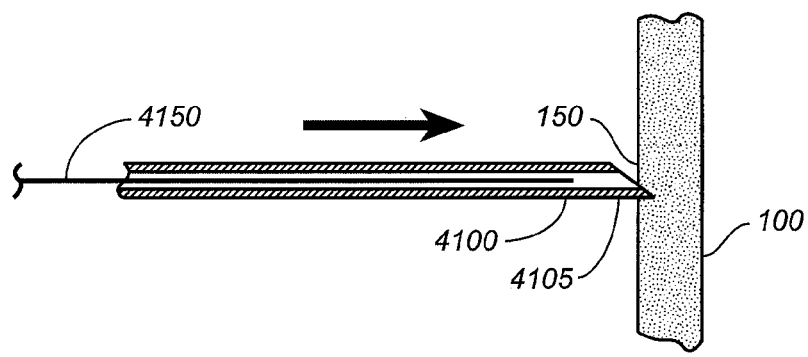
FIGS. 4A-4O are schematic partial cross-sectional side views showing one embodiment of a system and method for accessing space adjacent the serosa of the stomach through the esophagus for delivering items through the wall of a stomach, such as the electronics anchor shown in FIGS. 2A-2D or the electrode anchor shown in FIGS. 3A-3D.
Figure 4B:
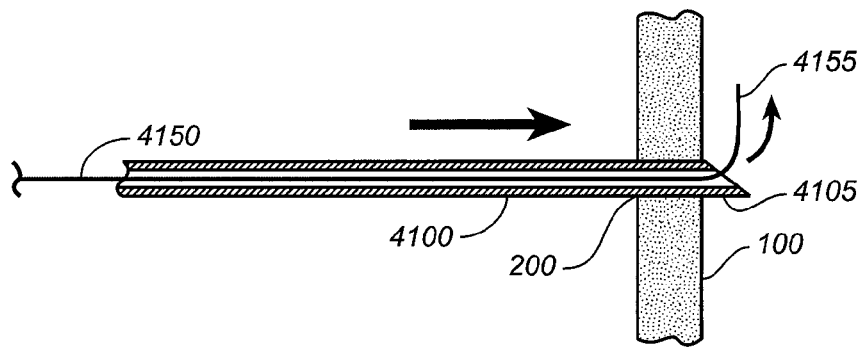
FIG. 4P shows one embodiment of a system 4000 for accessing space adjacent a serosa of a stomach through an esophagus.

FIGS. 4A and 4B illustrate the distal end 4105 of a needle 4100 used to pierce a stomach wall 100 from within the stomach to position a distal end 4155 of a guidewire 4150 through the stomach wall and form an opening 200. The proximal ends (not shown) of the needle 4100 and guidewire 4150 are positioned outside of a patient, typically, through the esophagus of the patient. Endoscopic visualization may be used to identify an anchor implantation site 150 in the stomach 100. Additionally or alternatively, fluoroscopic imaging may be used when piercing the stomach wall and/or positioning the guidewire as described herein. Once the stomach wall 100 is pierced with the needle 4100, the guidewire 4150 is positioned through the stomach wall 100 and preferably into a space adjacent the serosa of the stomach, e.g. the peritoneal cavity.

Figure 4C:
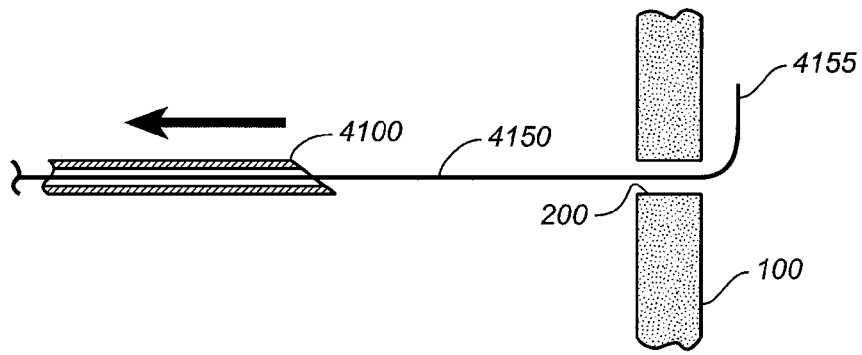

As shown in FIG. 4C, the needle 4100 is then removed leaving the guidewire 4150 in place through the stomach wall.

Figure 4D:
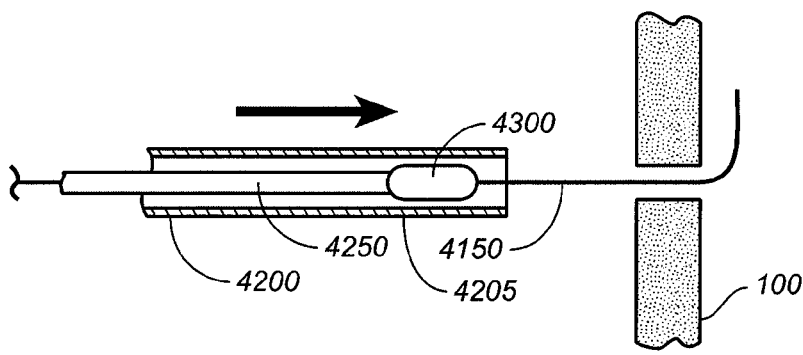
Figure 4E:
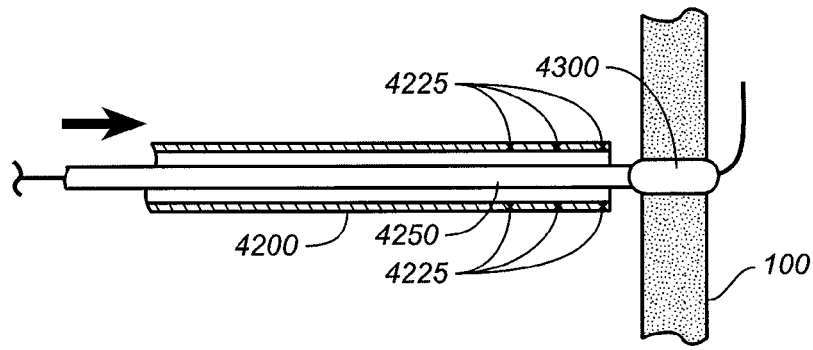

As shown in FIG. 4D, a balloon catheter 4250 comprising an expandable distal end or balloon 4300 and enclosed by sheath 4200 having a distal end 4205, is guided on the guidewire 4150 to the implantation site 150. As shown in FIG. 4E, the balloon 4300 is advanced through the sheath 4200 so that it is positioned in the stomach wall 100. The length of the balloon 4300 is sized so that it is longer than the stomach wall thickness. For example, in a typical stomach wall thickness of about 4 mm, the balloon 4300 may have a length of greater than approximately 4 mm. Thus, when the balloon 4300, is properly positioned, a portion of the balloon 4300 extends distally out of the stomach wall and a portion extends proximally into the stomach. The balloon may include visual or radiopaque markers that enable visualization of the balloon positioning. While balloons are disclosed herein for dilating the opening formed in the stomach, other expandable members may be used to dilate an opening through the stomach wall at the attachment site.

Figure 4F:
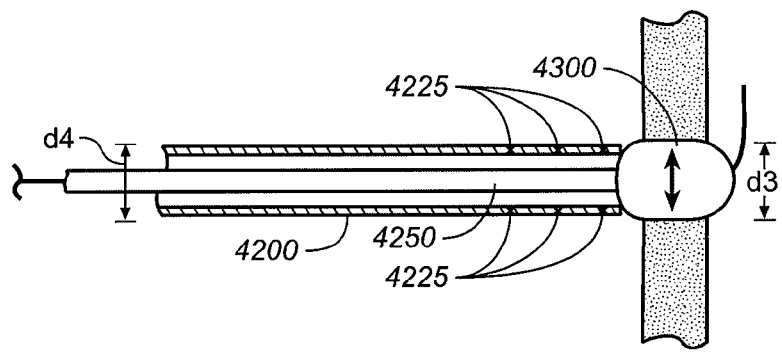
Figure 4G:
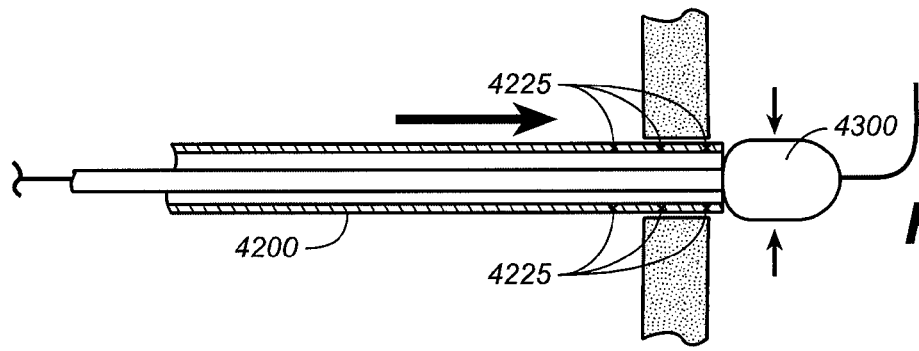

As illustrated in FIG. 4F, the balloon 4300 is inflated to dilate the opening 200 formed through the stomach wall 100 at the implantation site 150. The inflated outer diameter d3 of the balloon 4300 is greater than the outer diameter d4 of the sheath 4200. The balloon 4300 dilates the opening to a size in a range from about 2 mm to about 5 mm, but is not so limited. An initial period of inflation of the balloon 4300 at a first pressure will expand the hole in the stomach wall. As an example of duration and pressure, a first pressure e.g., of a pressure greater than 5 atmospheres for 45 seconds or longer may be sufficient to expand the hole in the stomach wall. In the next step, the distal end 4205 of the sheath 4200 will be engaged against the proximal end of the balloon, and both balloon and sheath are advanced in unison through the hole in the stomach. To facilitate this process, the balloon pressure may be slightly decreased while still maintaining the outer diameter d3 of the balloon 4300 greater than the outer diameter d4 of the sheath 4200. During this process, the balloon 4300 will become translatable through the hole in the stomach. FIG. 4G shows both balloon 4400 and sheath 4200 having crossed through the transgastric pathway 200 and the sheath distal end 4205 is approximately about 0.75 inches through the stomach wall, but this distance is not so limited. The distance the sheath is advanced may be determined with radiopaque markers 4225 (or visible markers if an endoscope is used for placement) positioned at a desired distance along the sheath 4200.

Figure 4H:
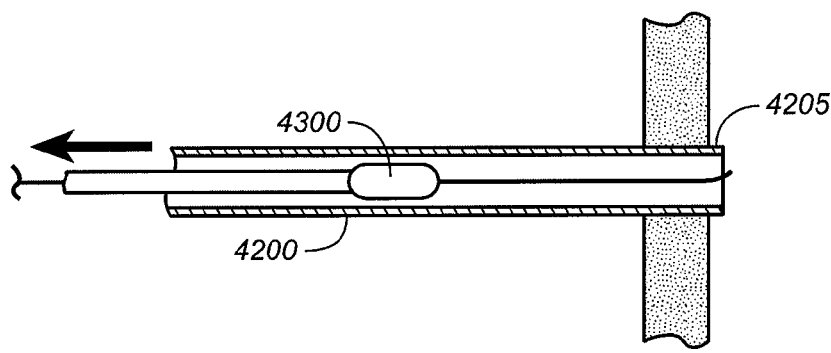

Once in position, as illustrated in FIG. 4H, the balloon 4300 is deflated and the balloon catheter 4250 is withdrawn from the sheath 4200. The sheath 4200 now provides a delivery conduit between the esophagus and the space adjacent the serosa of the stomach or peritoneal cavity. If a larger delivery conduit is required, a crossing catheter may be exchanged for the sheath as discussed below.

Figure 4I:
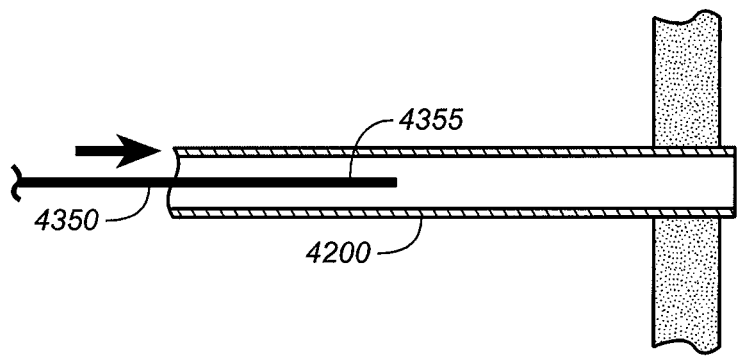
Figure 4J:
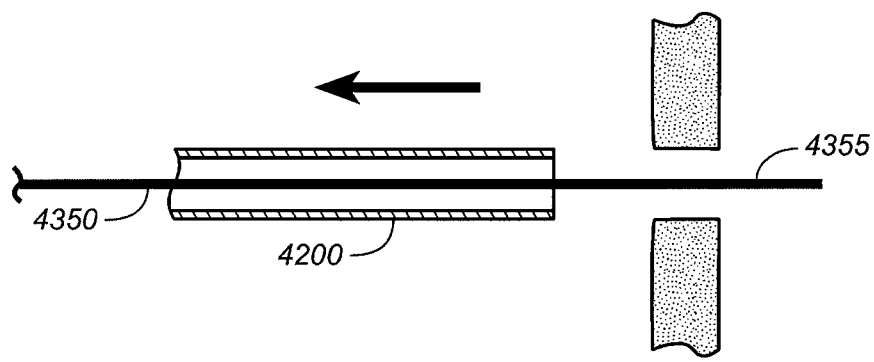
Figure 4K:
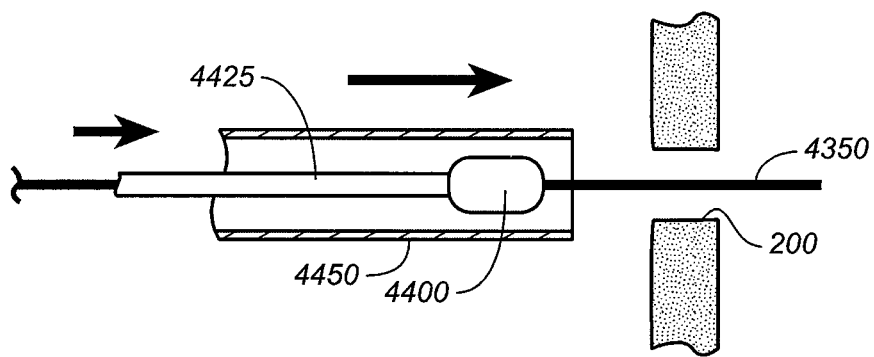
Figure 4L:
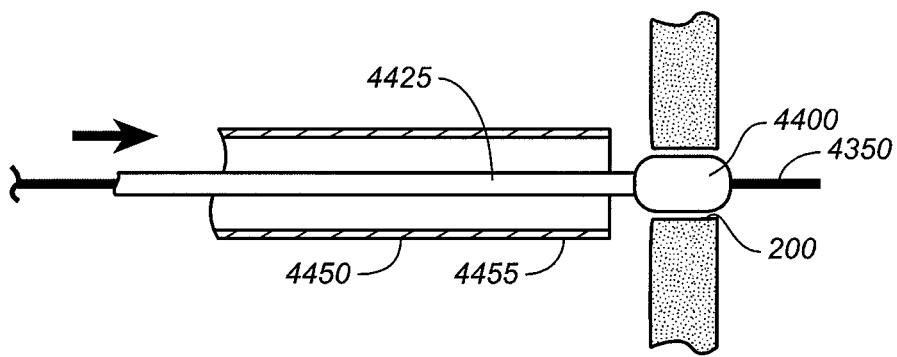
Figure 4M:
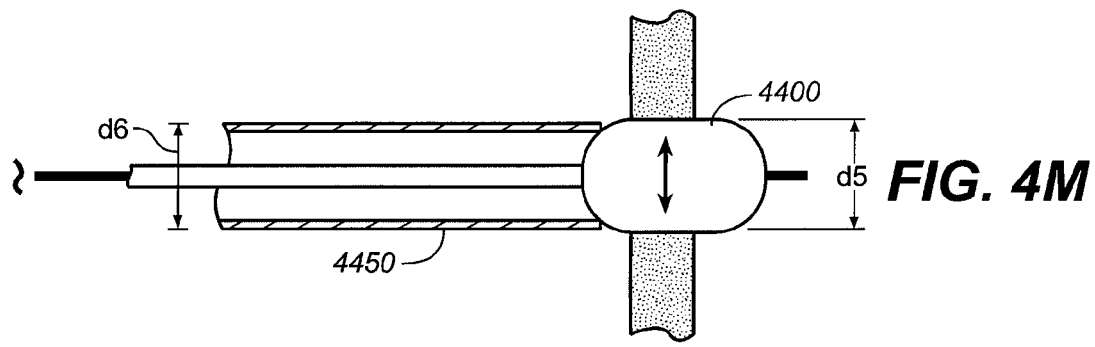
Figure 4N:
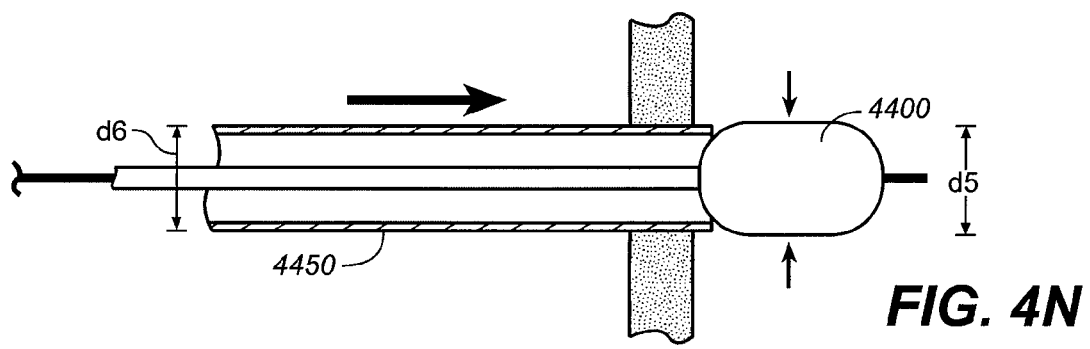
Figure 4O:
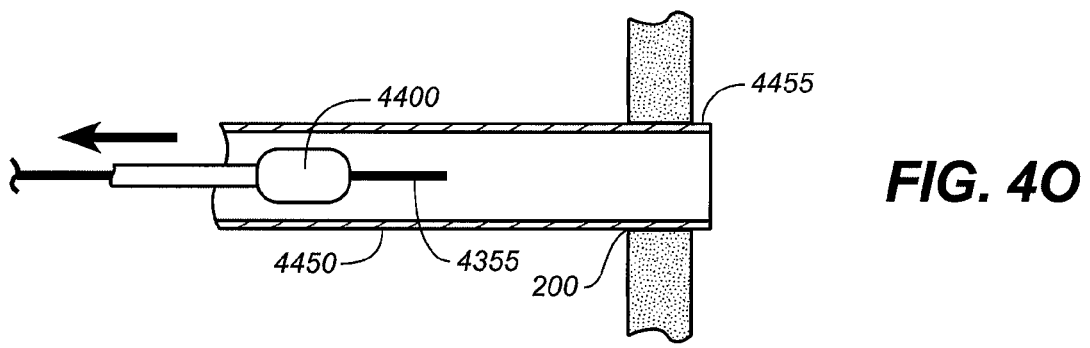

As illustrated in FIG. 4I, a larger diameter guidewire 4350 having a distal end 4355 is inserted through the sheath 4200 and through opening 200 in stomach 100. The sheath 4200 is then removed (FIG. 4J). The larger diameter guidewire 4350 supports and guides a larger diameter balloon 4400 on balloon catheter 4425, along with a crossing catheter 4450 with a distal end 4455 larger in diameter than the sheath 4200, into position adjacent the dilated opening 200 (FIG. 4K). During the next process, the crossing catheter 4450 will be advanced through the hole in the stomach 200, serving as a delivery conduit for the electronics anchor 2000 and the electrode anchor 3000. The balloon 4400 is positioned in the stomach opening 200 in a similar manner as balloon 4300 was (FIG. 4L). The balloon 4400 is then inflated to further dilate the opening 200 (FIG. 4M). The duration and pressure of this inflation may be similar to that used for the first balloon 4300. The diameter d5 of the inflated balloon 4400 is slightly larger than the outer diameter d6 of the crossing catheter 4450. The balloon 4400 dilates the opening to a size in a range from about 4 mm to about 10 mm, but is not so limited. After the initial inflation duration and pressure, the balloon pressure may be decreased to allow translation of the balloon through the hole 200 in the stomach wall, as was performed for the initial balloon. The inflated balloon 4400 and the crossing catheter 4450 are advanced in unison through opening 200 (FIG. 4N). The balloon 4400 is then deflated and removed from the crossing catheter 4450 and the distal end 4455 of the crossing catheter is left in place through the hole 200 (FIG. 4O). The crossing catheter 4450 is sized to accommodate passing of items to the peritoneal cavity, such as the electronics anchor 2000 and electrode anchor 3000 discussed below. In one embodiment, the inner diameter of the crossing catheter 4450 is more than about 5 mm.

Figure 4P:
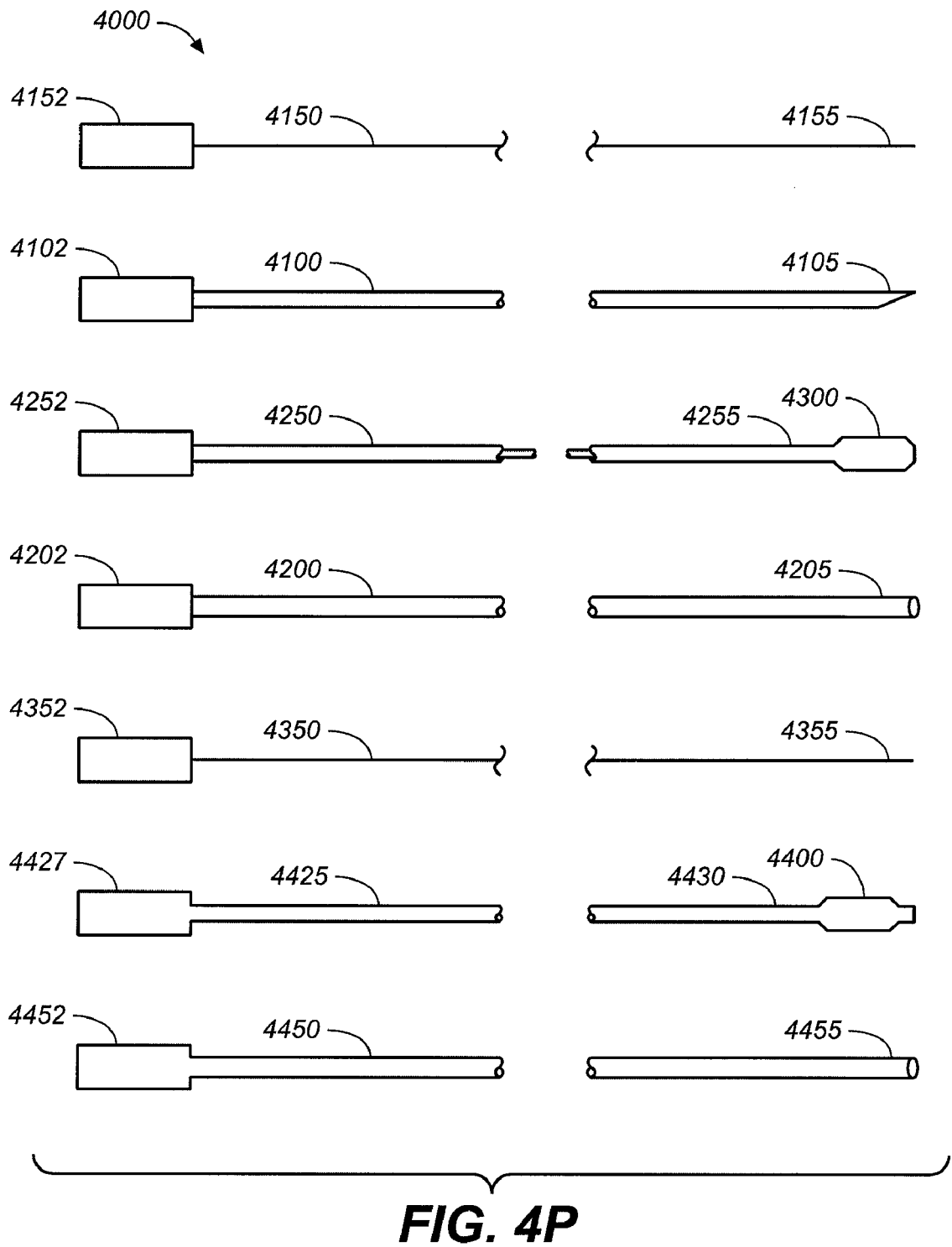

FIG. 4P shows one embodiment of a system 4000 for accessing space adjacent a serosa of a stomach through an esophagus. The system 4000 includes a needle 4150, a first guidewire 4100, a first balloon catheter 4250, a sheath 4200, a second guidewire 4350, a second balloon catheter 4425 and a crossing catheter 4450. The needle 4150 has a proximal end 4152 and a distal end 4155, the distal end is designed for piercing. The first guidewire 4100 has a proximal end 4102 and a distal end 4105, and is sized to slide through a lumen of the needle 4150. The first balloon catheter 4250 has a proximal end 4252 and an expandable first balloon 4300 on a distal end 4255. The first balloon catheter 4250 includes an inner lumen sized to slide over the first guidewire 4150. The sheath 4200 is designed to slide over the first balloon catheter 4250, with an outer diameter less than the expanded diameter of the first balloon 4300. The second guidewire 4350 has a proximal end 4352 and a distal end 4355. The second balloon catheter 4425 has a proximal end 4427 and an expandable second balloon 4400 on a distal end 4430. The second balloon catheter 4425 includes an inner lumen sized to slide over the second guidewire 4350. The crossing catheter 4450 has a proximal end 4452 and a distal end 4455. The crossing catheter 4450 includes an inner lumen sized to be delivery conduit through the esophagus of the patient to the space adjacent the serosa of the stomach or the peritoneal cavity.

Placement of the Electronics Anchor

Figure 5A:
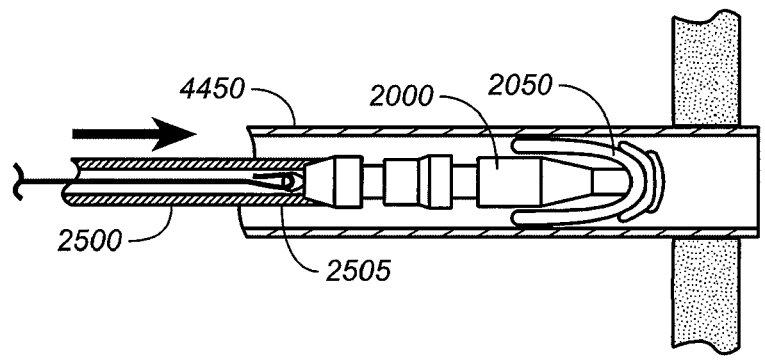
FIGS. 5A-5F are schematic partial cross-sectional side views showing one embodiment of a delivery system and method for delivering an electronics anchor shown in FIGS. 2A-2D through the wall of a stomach.
Figure 5B:
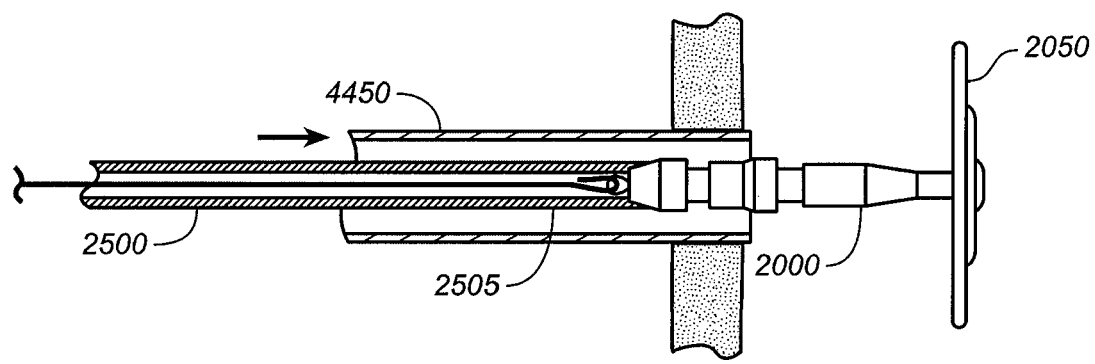
Figure 5C:
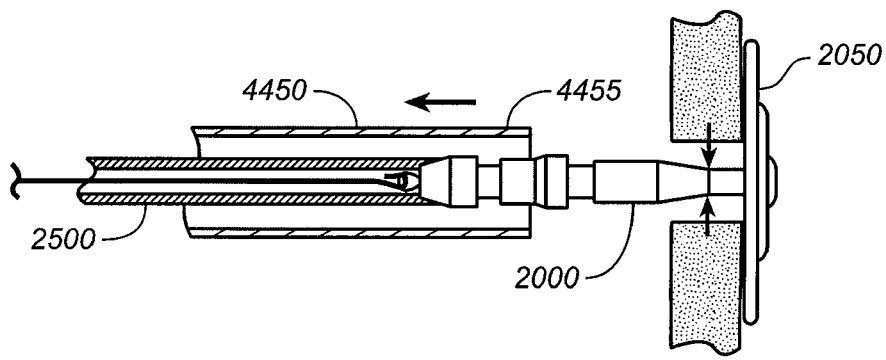
Figure 5D:
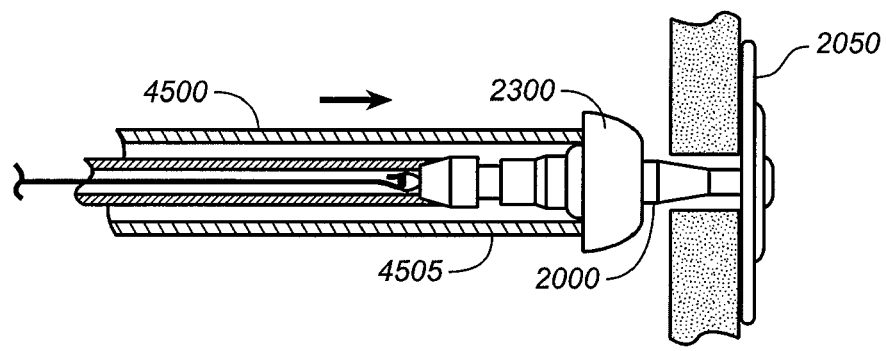
Figure 5E:
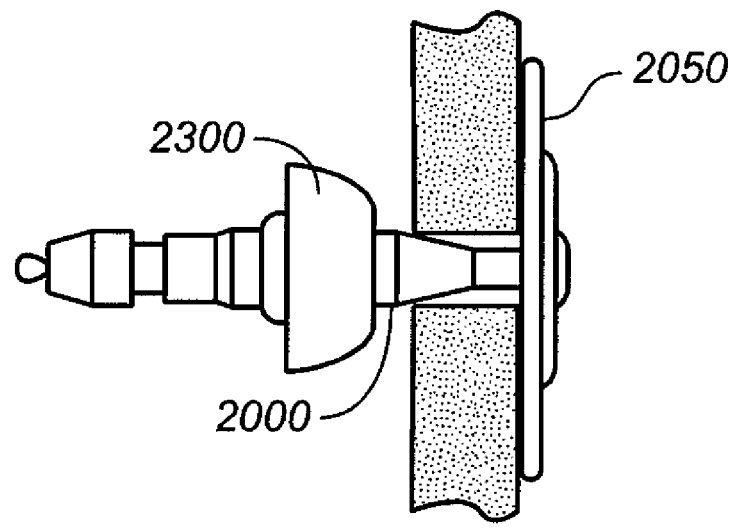
Figure 5F:
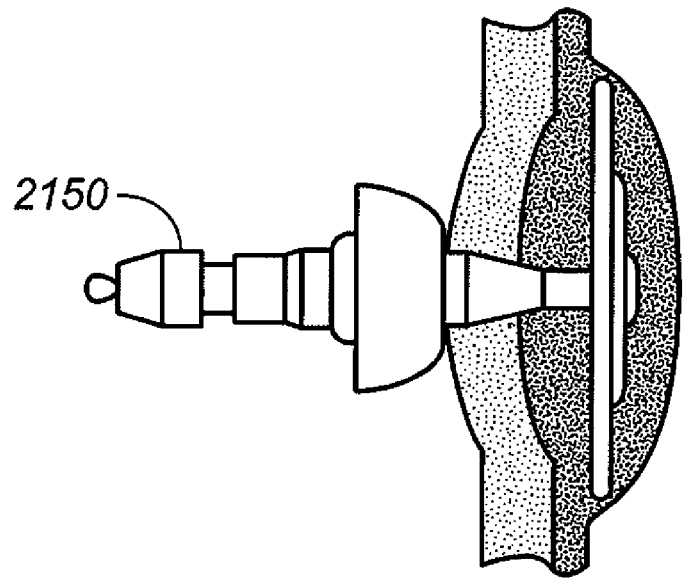

FIGS. 5A-5F illustrate an embodiment of methods and delivery devices for the placement of the electronics anchor 2000. The anchor 2000 is positioned into the crossing catheter 4450 with the distal anchor portion 2050 in a folded or compressed position. The anchor 2000 is pushed through the crossing catheter 4450 with a distal end 2505 of a guide element 2500 which is coupled to the proximal tapered end 2400 of the anchor 2000 (FIG. 5A). The distal anchor portion 2050 of the anchor 2000 is advanced through the crossing catheter 4450 until the distal anchor portion 2050 extends out of the distal end of the crossing catheter 4450 where it unfolds or expands (FIG. 5B). The crossing catheter 4450 is then withdrawn and the anchor portion 2050 of the anchor 2000 may be pulled into engagement with the outer wall of the stomach, using the guide element 2500 (FIG. 5C). A retaining element 2300 is positioned over the guide element 2500 outside of the subject's mouth and is advanced over the guide element 2500 using a distal end 4505 of a coaxial push element or push element 4500 until the detent mechanism 2350 (FIG. 2B) engages the first detent 2200 of the anchor 2000 (FIG. 5D). The push element 4500 and guide element 2500 are then removed and the anchor remains in the opening (FIG. 5E). A purse string stitched suture may also be used to cinch up the hole in the stomach wall around the anchor. In some cases, the anchor 2000 may be left in position for a period of time (e.g. two to four weeks, or more than two weeks) until the stomach has healed (FIG. 5F). The guide element 2500 is then reinserted and attached to the proximal end 2150 of the anchor 2000 for delivery and attachment of the IPG 10 to the electronics anchor 2000, described in more detail with respect to FIG. 7A.

Placement of the Electrode Lead Anchor

Figure 6A:
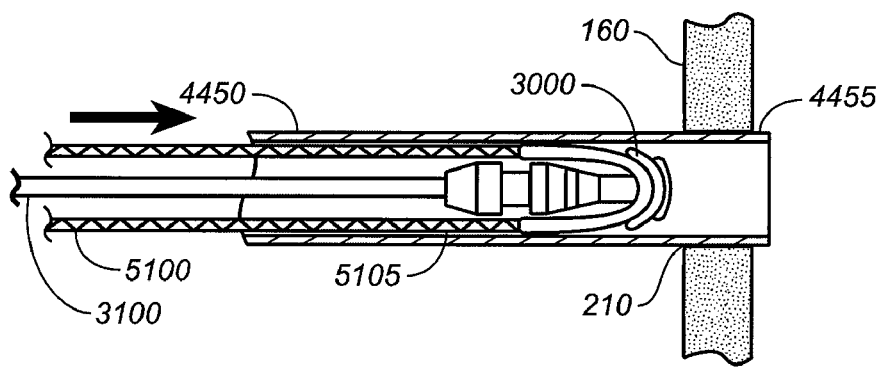
FIGS. 6A-6C are schematic partial cross-sectional side views showing one embodiment of a delivery system and method for delivering an electrode anchor shown in FIGS. 3A-3D through the wall of a stomach.
Figure 6B:
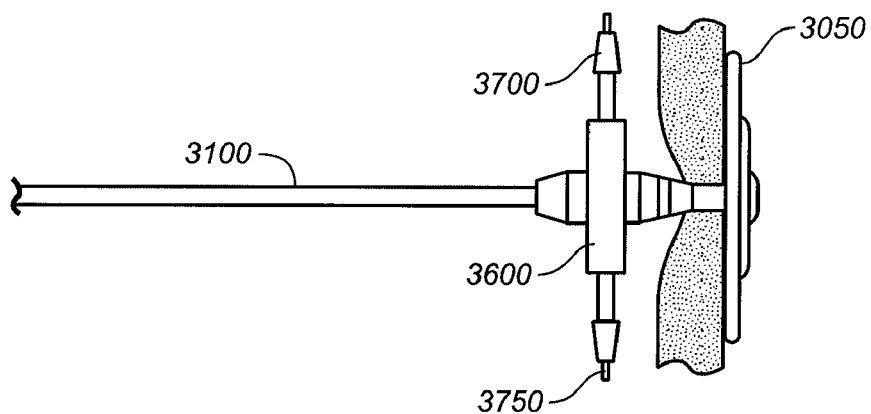
Figure 6C:
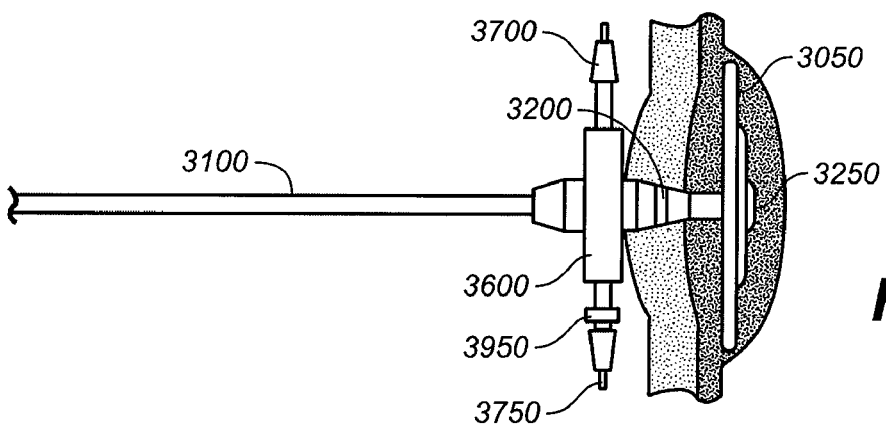

The placement of the electrode lead anchor 3000 may be deployed in a similar manner as the electronics anchor 2000 described above. In deploying the electrode lead anchor 3000, as illustrated in FIGS. 6A-6C, a dilated opening 210 at a second location 160 is first formed in the stomach wall 100 for deployment in a manner similar as that described with respect to FIGS. 4A-4O herein. Deployment site for the electronics anchor 2000 may for example be at a location on the fundus, and for example, for the electrode anchor 3000 the body or antrum.

As illustrated in FIG. 6A the electrode lead anchor 3000 including the lead portion 3100 is positioned in a crossing catheter 4450. A distal end 5105 of a push element 5100 is positioned over the lead 3100 and is used to advance the anchor 3000 through the crossing catheter 4450 and out the distal end 4455.

As illustrated in FIG. 6B, the anchor portion 3050 is positioned outside the stomach wall. The elongate portion extends through the stomach wall with at least one of electrodes 3200, 3250 in electrical contact with the stomach wall. The retaining element 3600 is positioned over the flexible lead portion 3100 and is retained on the elongate member with a detent mechanism similar to the detent mechanism 2350 described above with respect to anchor 2000. In some embodiments, the retaining element 3600 is spaced away from the inside of the stomach wall to permit the healing process to occur (FIG. 6C).

Figure 6E:
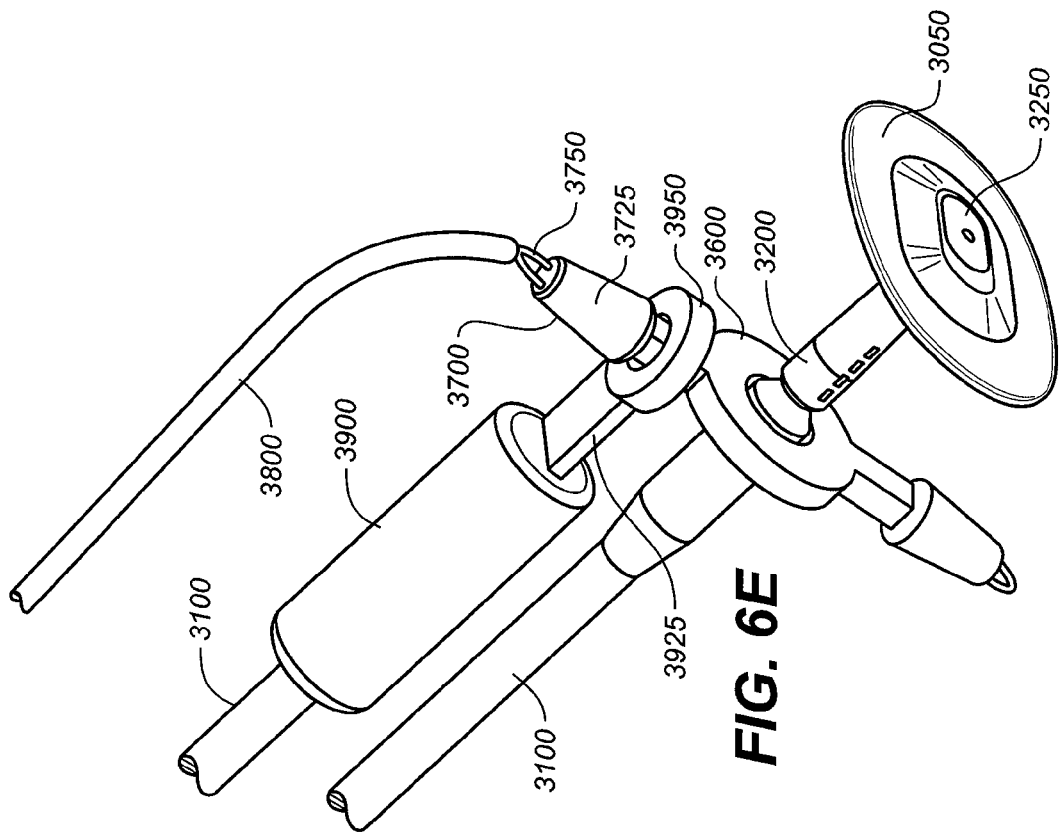
FIG. 6E is a perspective view of the electrode anchor and retaining element with the end of the electrode lead with a temporary capped connector attached to the retaining element.
Figure 6D:
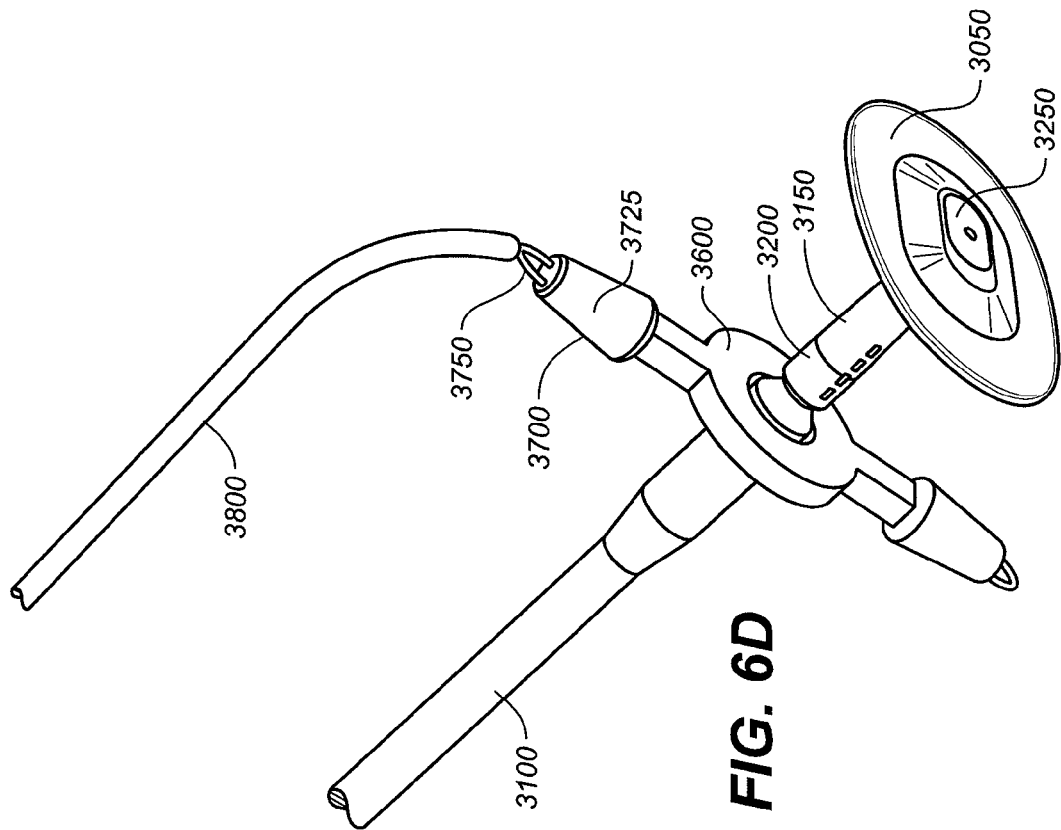
FIG. 6D is a perspective view of the electrode anchor and retaining element with a guide element attached to the anchor used to attach the temporary cap.
Figure 6F:
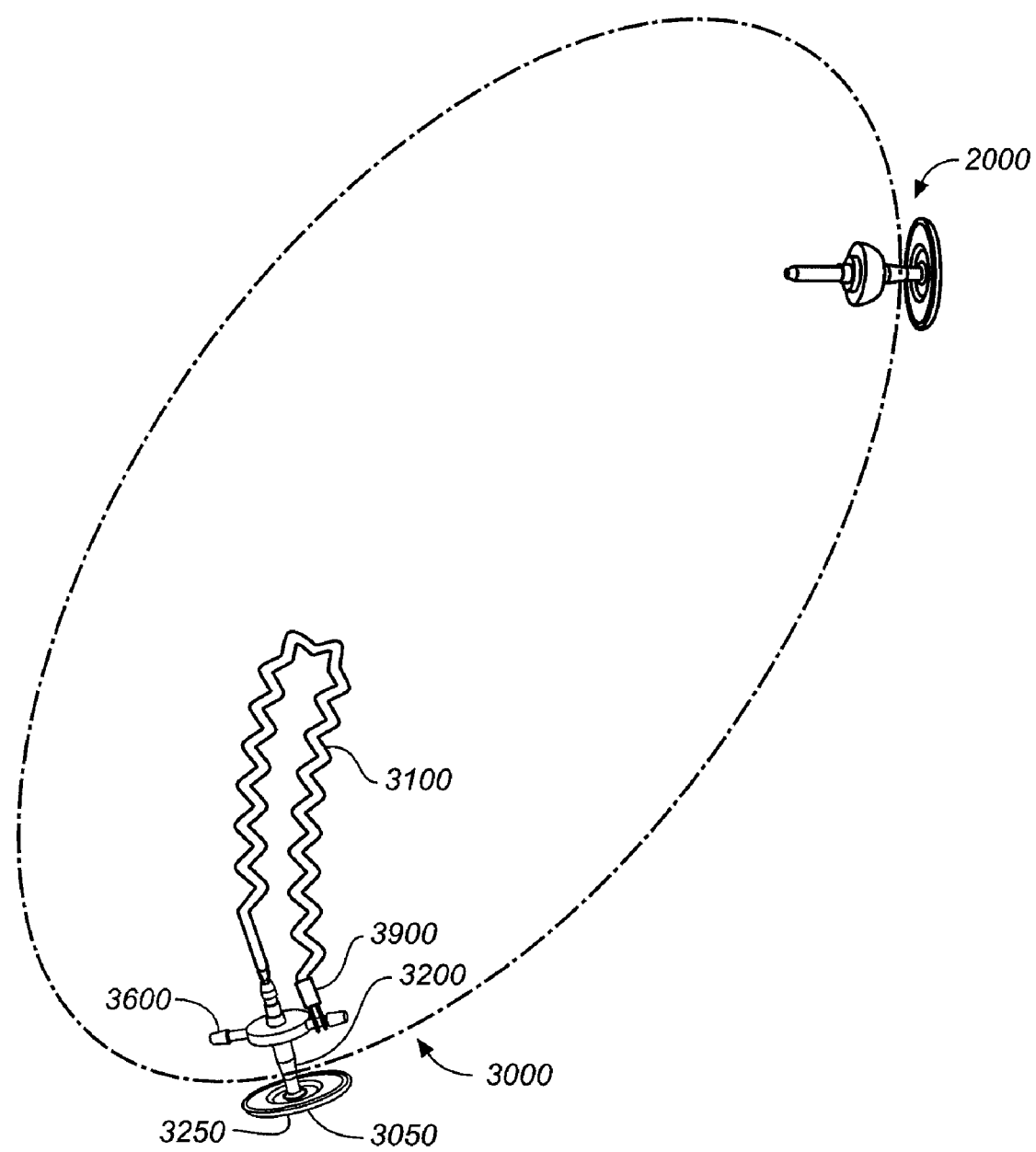
FIG. 6F is a schematic illustration showing the electrode lead with the temporary capped connector attached to the electrode anchor in the stomach.

As mentioned previously, the flexible lead portion 3100 is coupled with the retaining element 3600 during the healing process. FIGS. 6E and 6F illustrate attachment of the proximal end of the flexible lead portion 3100 to the retaining element 3600. FIG. 6E illustrates a temporary cap 3900 attached to the connector end 3425 of the lead portion 3100. In one embodiment, the electrode lead anchor 3000 is implanted and left in place a few weeks before the IPG 10 is delivered to the stomach and attached to the flexible lead portion 3100. In this case, the temporary cap 3900 may be secured over the proximal lead connector 3400, to seal the connectors 3450 during the healing process. To ensure that the flexible lead portion 3100 is not unsecured and free floating in the stomach, the temporary cap 3900 will be attached to the retaining element 3600 while the anchor heals in place for a several week period, as illustrated in FIG. 6F. This attachment forms the lead portion 3100 into a closed loop and prevents the lead from being tied into a knot during the daily stomach contractions associated with digestion.

Referring back to FIG. 6D, a delivery tool 3800 is shown attached to a loop hook 3750 of retaining element 3600. The delivery tool 3800 includes a hook (not shown) which is advancable from its distal end to engage the loop hook 3750. The hook (not shown) is then retracted into the delivery tool 3800 so that the delivery tool 3800 is snug against the retaining element 3600. The delivery tool 3800 is then used to deliver the proximal end of the flexible lead portion 3100 to the retaining element 3600.

FIG. 6E shows the temporary cap 3900 having a flat extender portion 3925 and a connector ring 3950. The connector ring 3950 is configured to couple with arms 3700. To connect the temporary cap 3900 to the arms 3700 of the retaining element 3600, the proximal end of the delivery tool 3800 is inserted through the connector ring 3950 and advanced along the delivery tool 3800 toward the retaining element 3600. Thus, the delivery tool 3800 is used to guide the connector ring 3950 of the temporary cap 3900 onto the arm 3700 of the retaining element 3600 to secure the connector end 3425 (within cap 3900) of the lead to the retaining element 3600, thus effectively forming a closed loop of the lead portion 3100, as illustrated in FIG. 6F. The ring 3950 is relatively flexible and can be pushed over the conically tapered portion 3725 of the arm 3700 into a detent in the arm 3700 so that the ring 3750 is secured onto the arm 3700.

Figure 7A:
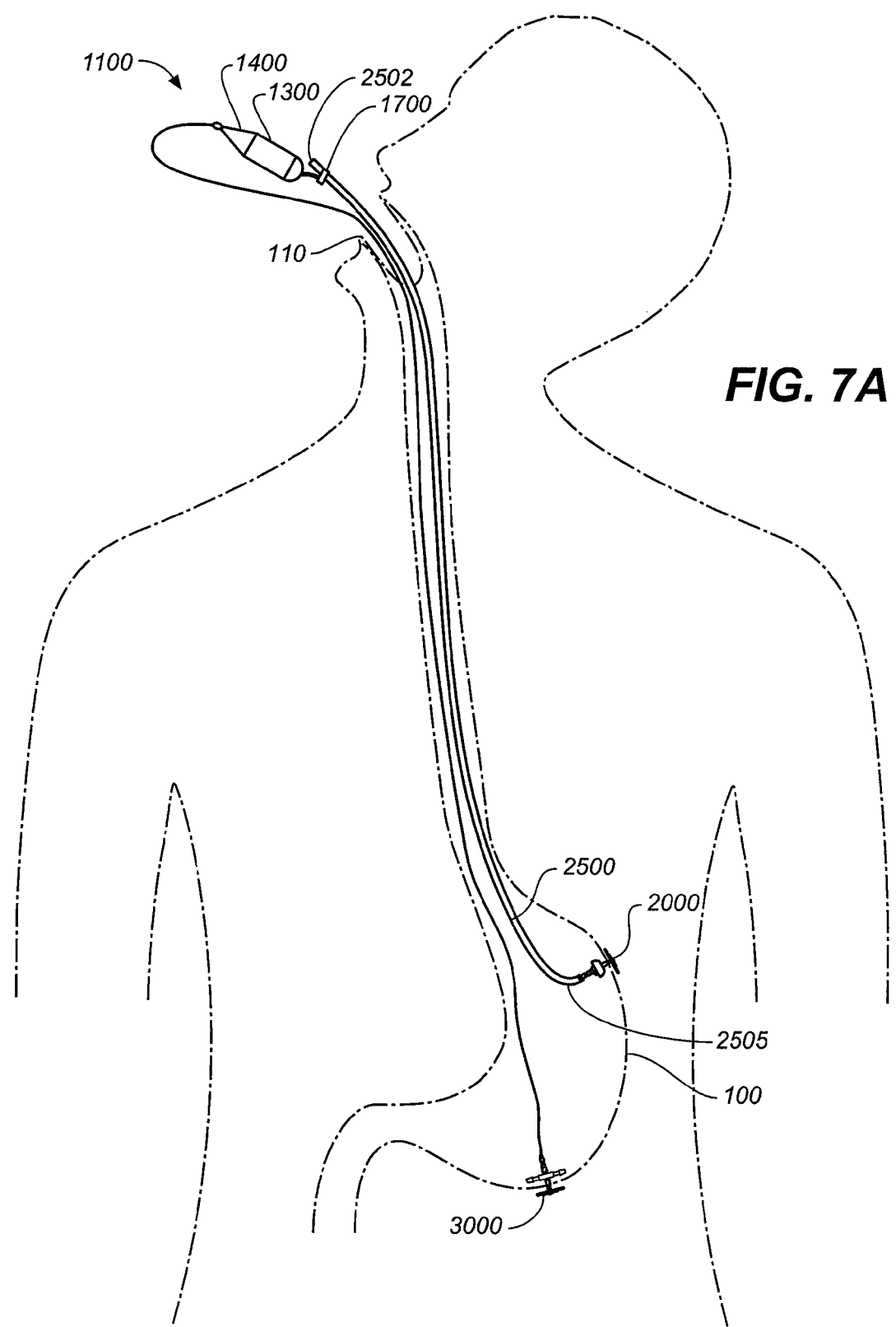
FIGS. 7A and 7B are schematic illustrations of the stimulation system being implanted in the stomach.

After the healing process has occurred, the flat extender portion 3925 of the cap 3900 is cut, freeing the proximal end of the lead 3425 of the flexible lead portion 3100 with the temporary cap 3900 still attached. Using endoscopic methods, the connector end 3425 of the flexible lead portion 3100 may then be pulled through the esophagus out of the mouth where the temporary cap 3900 is removed and the connector end 3425 is coupled to the connector 1800 of the header 1400 of the housing 1300 as shown in FIG. 7A.

Placement of the Stimulator within the Stomach

Figure 7B:
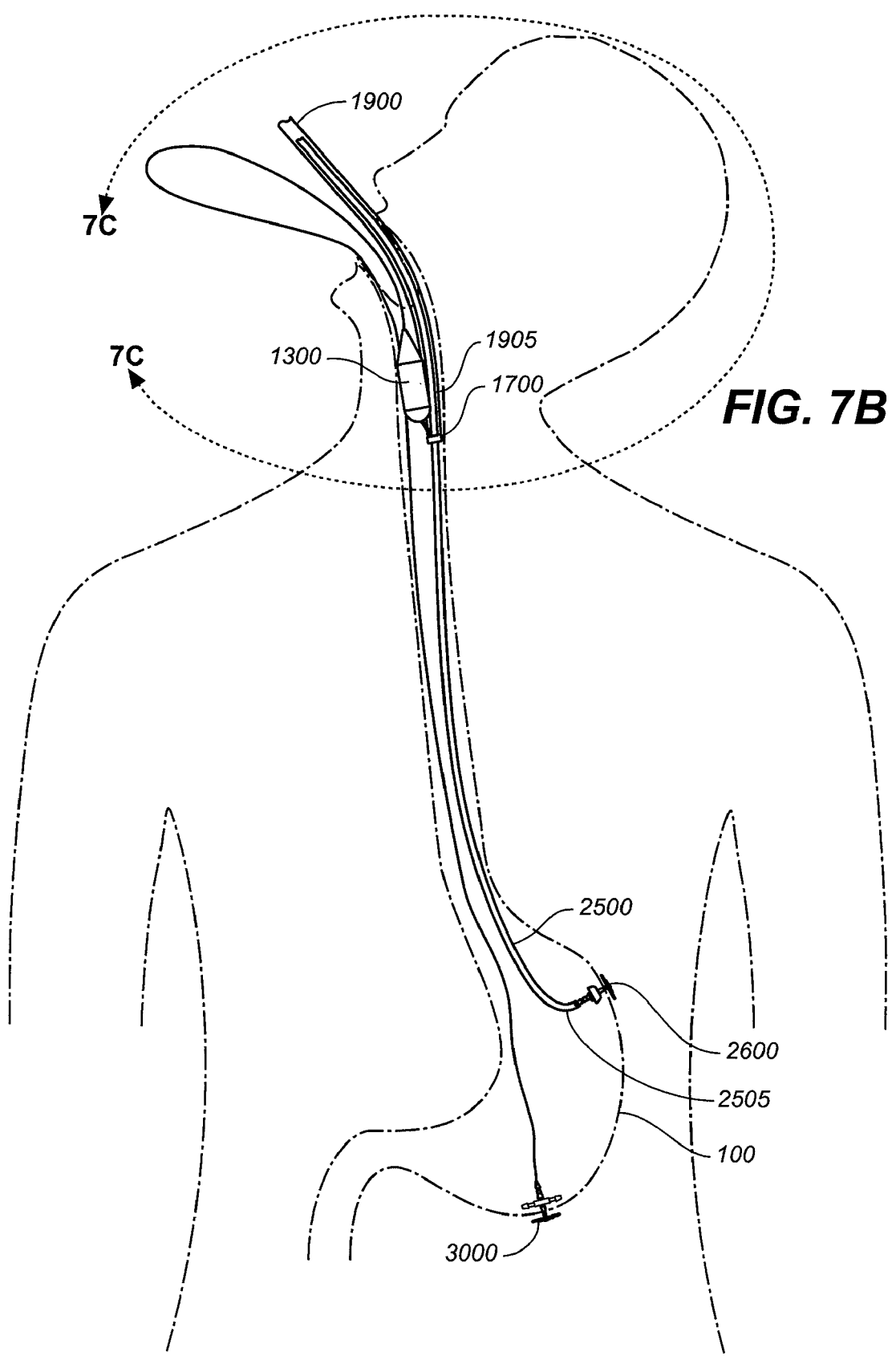
Figure 7C:
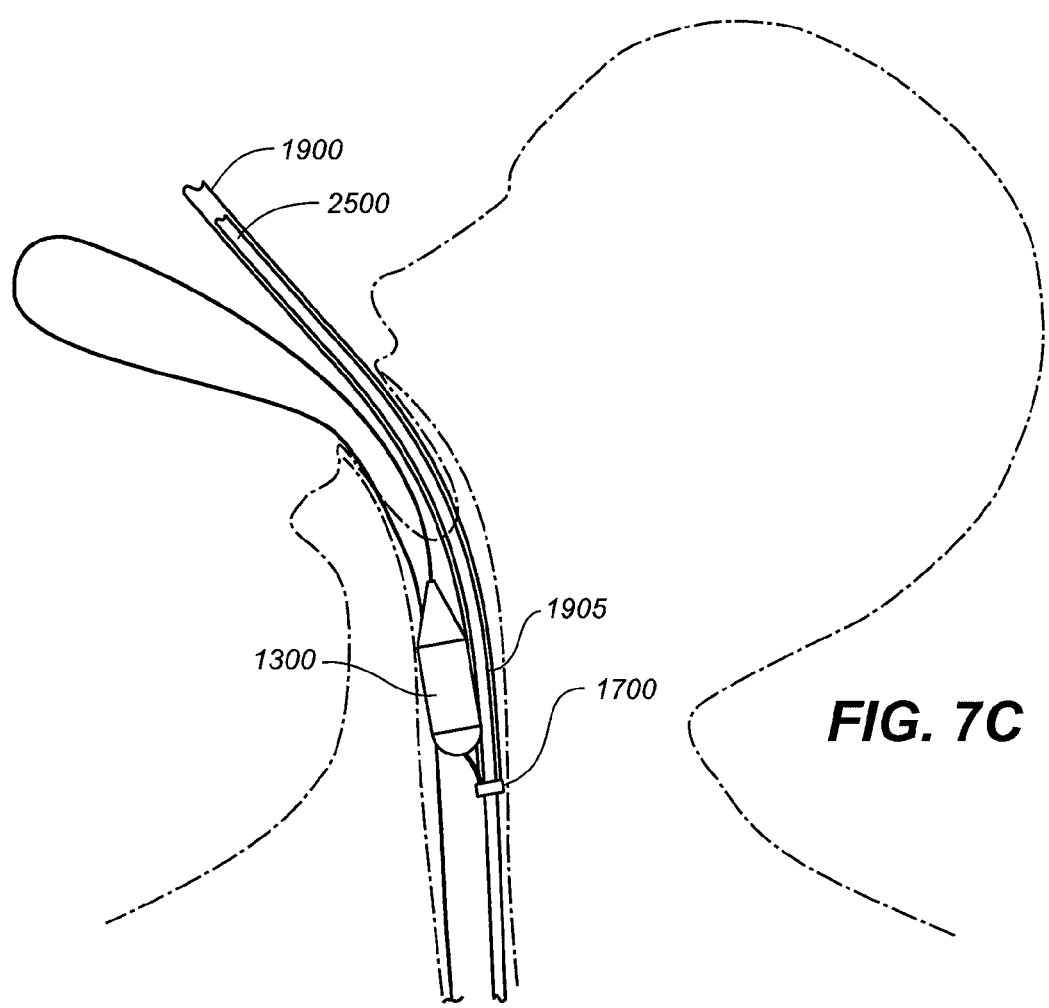
FIG. 7C is an enlarged view of a portion of FIG. 7B.
Figure 7D:
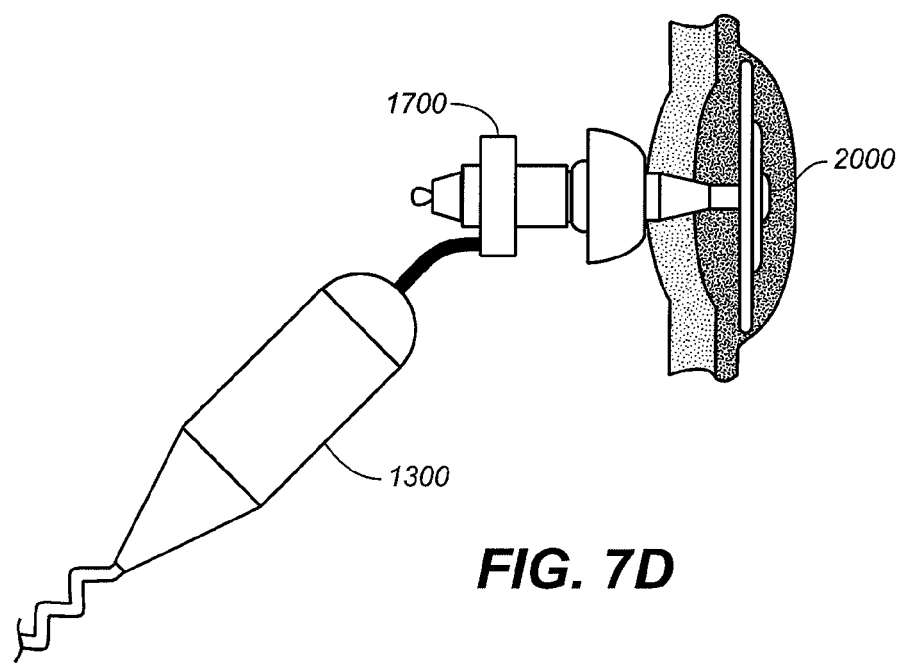
FIG. 7D is schematic illustrations of the stimulation system attached to the electrode anchor in the stomach.

FIGS. 7A-7D schematically illustrate the IPG 10 being positioned into the stomach after the electronics anchor 2000 and electrode lead anchor 3000 have been installed (see FIG. 2A through FIG. 6F herein). A guide element 2500 having a proximal end 2502 and a distal end 2505 is used to guide the IPG 10 into a position where it is attached to the electronics anchor 2000. A connector element 1700 attached to the IPG 10 is positioned over the proximal end 2502 of guide element 2500 when the IPG 10 is outside the subject's mouth 110. At the same time, the connector 3400 of flexible lead portion 3100 is attached to the connector 1800 within header 1400 of IPG 10 while outside of the mouth (FIG. 7A, see also FIGS. 1, 3C and 3D). As illustrated in FIGS. 7B-7C the connector element 1700 is pushed with a distal end 1905 of a push element 1900, such as coaxial coil, over the guide element 2500, thereby also pushing the housing 1300 and flexible lead portion 3300 into the stomach. The guide element 2500 acts as a guide rail with a compression element to guide the connector element 1700 to the proximal end of the electronics anchor 2000, where the connector element 1700 couples to a detent 2250 (see FIG. 2D). The connector may be constructed of a metal material having an opening having an inner diameter with an o-ring positioned around the inner diameter. The o-ring 1750 engages the detent 2250 to secure the connector element 1700 to the electronics anchor 2000 as described herein. The o-ring 1750 or detent 2250 may be constructed of a corrosion resistant polymer such as a fluoroelastomer, e.g., Viton® or Kalrez®. The IPG 10 is thus implanted within the stomach, anchored to the stomach wall by the electronics anchor 2000 and able to stimulate the stomach wall by use of the electrode lead anchor 3000.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of accessing space adjacent a serosa of a stomach through an esophagus of a patient, the method comprising:
    piercing the stomach wall from within the stomach forming an opening in a stomach wall between the stomach and the space adjacent the serosa of the stomach;
    positioning a first balloon on a first balloon catheter within the opening;
    inflating the first balloon and dilating the opening to a first diameter;
    advancing a sheath and the first balloon catheter in unison distally through the opening until the sheath extends through the stomach wall;
    deflating the first balloon; and
    withdrawing the first balloon catheter through the sheath.

2. The method of claim 1, wherein the first balloon is sized to span a thickness of the stomach wall and dilates the opening to a size in a range from about 2 mm to about 5 mm.

3. The method of claim 1, wherein inflating the first balloon includes inflating the first balloon for a duration of more than about 45 seconds and to a pressure of greater than approximately 5 atmospheres.

4. The method of claim 1, further comprising decreasing the balloon pressure sufficiently to allow the first balloon to be translatable after dilation and prior to advancing the sheath and first balloon through the opening.

5. The method of claim 1, wherein the sheath has an outer surface adjacent an outer surface of the balloon when the sheath and the balloon are advanced in unison.

6. The method of claim 1, wherein the distal end of the sheath is advanced more than approximately 0.75 inches beyond the stomach wall.

7. The method of claim 1, wherein piercing the stomach wall comprises advancing a distal end of a hollow needle through the stomach wall while a proximal end of the needle extends out of the esophagus of the patient, advancing a first guidewire through the needle and the opening and into the space and withdrawing the needle over the first guidewire.

8. The method of claim 1, further comprising:
    positioning a second balloon within the opening, the second balloon being sized to span the stomach wall;
    inflating the second balloon and further dilating the opening to a second diameter;
    advancing a crossing catheter and the second balloon catheter in unison through the opening until the crossing catheter extends through the stomach wall;
    deflating the second balloon; and
    withdrawing the second balloon catheter through the crossing catheter.

9. The method of claim 8, wherein positioning a second balloon within the opening comprises:
    advancing a second guidewire through the sheath and into the space adjacent the serosa of the stomach;
    withdrawing the sheath over the second guidewire, leaving the second guidewire in place through the opening; and
    advancing the crossing catheter and the second balloon catheter with the second balloon over the second guidewire.

10. The method of claim 8, wherein inflating the second balloon includes inflating the second balloon for a duration of more than 45 seconds to a pressure of greater than approximately 5 atmospheres.

11. The method of claim 8, further comprising decreasing balloon pressure sufficiently to allow the second balloon to be translatable prior to advancing the crossing catheter and second balloon through the opening.

12. The method of claim 8, wherein the distal end of the crossing catheter is advanced more than about 0.75 inches through the stomach wall.

13. The method of claim 8, further comprising imaging one or more of the distal end of the first balloon catheter, the second balloon catheter, the sheath, and/or the crossing catheter.

14. The method of claim 8, wherein the second guidewire has a larger diameter than the first guidewire.

15. The method of claim 8, wherein the crossing catheter has an inner diameter of more than about 5 mm.

16. The method of claim 8, wherein the proximal end of the advanced crossing catheter extends out of the esophagus of the patient.

17. The method of claim 16, further comprising employing the crossing catheter as a delivery conduit through the esophagus of the patient to the space adjacent the serosa of the stomach or the peritoneal cavity.

* * * * *